(12) United States Patent
Hicks et al.

(10) Patent No.: US 8,334,973 B2
(45) Date of Patent: Dec. 18, 2012

(54) OPTICAL EMISSION SPECTROSCOPY DEVICE

(75) Inventors: Thomas P. Hicks, Lafayette, IN (US); Donald DeWitt, Syracuse, IN (US); David Martin Taylor, Lincolnshire, IL (US); Wayne Skinner, Lafayette, IN (US)

(73) Assignee: Steiner Enterprises, Inc., Lafayette, IN (US)

( * ) Notice: Subject to any disclaimer, the term of this patent is extended or adjusted under 35 U.S.C. 154(b) by 401 days.

(21) Appl. No.: 12/724,996

(22) Filed: Mar. 16, 2010

(65) Prior Publication Data
US 2010/0238437 A1    Sep. 23, 2010

Related U.S. Application Data

(60) Provisional application No. 61/161,211, filed on Mar. 18, 2009.

(51) Int. Cl.
*G01J 3/30* (2006.01)
(52) U.S. Cl. .................................................. 356/311
(58) Field of Classification Search .................. None
See application file for complete search history.

(56) References Cited

U.S. PATENT DOCUMENTS

| 3,048,738 A | 8/1962 | Paul, Jr. |
| 6,396,583 B1 * | 5/2002 | Clare ........................... 356/436 |
| 2005/0194903 A1 | 9/2005 | Minamoto et al. |
| 2007/0152561 A1 | 7/2007 | Ono et al. |

* cited by examiner

*Primary Examiner* — Tu Nguyen
(74) *Attorney, Agent, or Firm* — Maginot, Moore & Beck, LLP

(57) ABSTRACT

A spectral analysis apparatus includes a light transmissive envelope, first and second electrodes, a sleeve, and first and second electrical contacts. The light transmissive envelope contains a fluid operable to emit light when electrically energized. The first electrode is disposed upon an external surface of an end portion of the envelope external to the envelope. The second electrode is disposed upon an external surface of a second end portion external to the envelope. The sleeve defines a cavity configured to removably receive the envelope. The electrical contacts are in communication with the cavity and are configured to electrically connect to the corresponding electrode when the envelope is within the sleeve. The electrical contacts are connectable to an electrical power supply and electrically energize the fluid when connected to the electrical power supply.

30 Claims, 21 Drawing Sheets

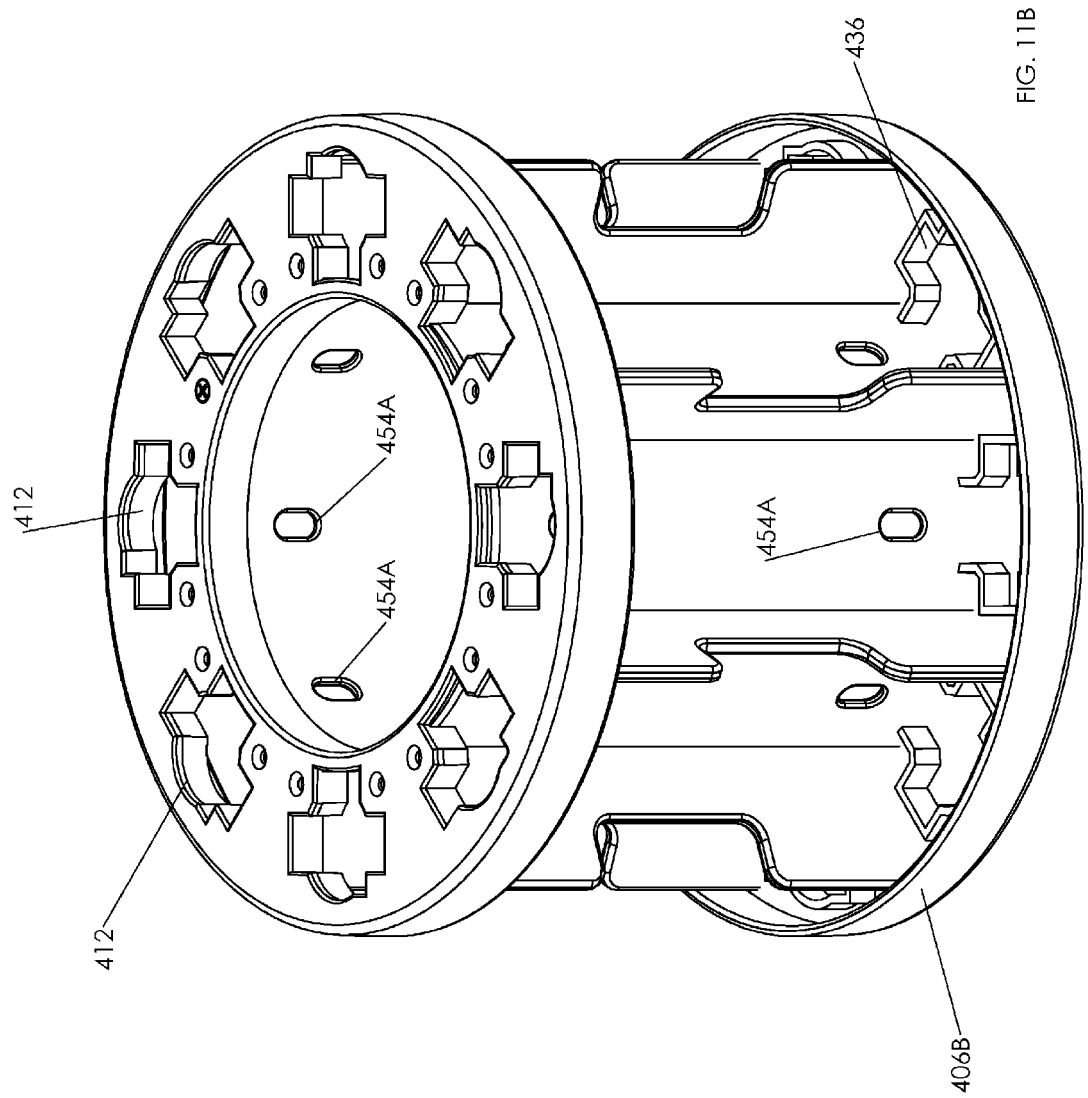

OPTICAL EMISSION SPECTROSCOPY DEVICE

CROSS REFERENCE TO RELATED APPLICATIONS

This application claims priority to U.S. Provisional application No. 61/161,211, filed on Mar. 18, 2009, and entitled "Electrodeless Spectrum Tube and Power Supply," the entire disclosure of which is incorporated herein by reference.

BACKGROUND

The present disclosure relates to optical emission spectroscopy devices, and more specifically to a spectroscopy device power unit and a fluid filled cartridge configured to emit light in response to being energized by the spectroscopy device power unit.

Optical emission spectroscopy devices, referred to herein as spectroscopy devices, electrically energize a fluid to cause the fluid to emit light. Spectroscopy devices typically include a power supply unit configured to receive a glass envelope containing a fluid. The power supply unit introduces an alternating current to the fluid contained by the glass envelope. In response to this alternating current the fluid emits light of a particular wavelength that is dependent on the elemental composition of the fluid. Some of these wavelengths are present in the visible light spectrum, while others can only be detected with specialized equipment.

Spectroscopy devices are often used in educational environments to introduce students to the field of spectrum analysis. In general, spectrum analysis is the process of identifying an unknown specimen fluid by comparing the wavelengths of light emitted by the specimen fluid with the wavelengths of light emitted by known fluids. Spectroscopy devices may also be useful to introduce students to the quantum physical model of the atom.

A prior art glass envelope 10, for use with a spectroscopy device, is depicted in FIG. 16. The envelope 10 includes electrodes 14, wires 18, contacts 22, and a fluid contained within an internal cavity 26. The electrodes 14 are positioned within the cavity 26 to provide electrical energy from a power unit (not illustrated) to the fluid. Connected to each electrode 14 is a wire 18 that penetrates the envelope 10 so that part of the wire is inside the cavity 26 and part of the wire is outside. Each wire 18 is connected to a respective electrical contact 22 mounted at opposite ends of the exterior of the envelope 10.

The power unit of known spectroscopy devices includes a power supply and two electrical sockets. The power supply is connected to a source of electrical energy, such as a wall outlet. The power supply generates a high voltage electrical signal that is connected to the electrical sockets. The fluid contained by the envelope 10 emits light when the envelope, and in particular the contacts 22, are connected to the electrical sockets.

Traditional spectroscopy devices, despite their educational attributes, often suffer from several deficiencies. First, to couple a glass envelope to the power unit, the glass envelope is handled directly by the user. Accordingly, there exits the potential that a user may drop the envelope causing it to break. Second, known glass envelopes for use with spectroscopy devices suffer from design weaknesses that limit the useful life of the envelopes. In particular, because the wires 18 penetrate the envelope 10, air from outside of the cavity 26 is often drawn into the envelope at the junction of the envelope and the wire, because is it is difficult to achieve a hermetic seal between the glass and the wire. Additionally, some fluids may react with the internal electrodes 14, which may cause the electrodes 14 to corrode or degrade and eventually become nonfunctional. Furthermore, the fluid may undergo a chemical change in response to prolonged exposure to the electrodes 14, thereby causing the fluid to exhibit unexpected characteristics. Moreover, the electrical sockets of known power units may become connected to electrical energy both when an envelope is received by the sockets and when an envelope is not received by the sockets, such that high levels of electrical safety must be practiced around known spectroscopy devices. What is needed, therefore, is an improved spectroscopy device.

SUMMARY

In accordance with the present disclosure, there is provided a spectroscopy device, referred to as a spectral analysis apparatus, which includes a light transmissive envelope, a first and second electrode, a sleeve, and a first and second electrical contact. The light transmissive envelope includes a first end portion and a second end portion and the envelope contains a fluid operable to emit light when electrically energized. The first electrode is disposed upon an external surface of the first end portion and is completely external to the envelope. The second electrode is disposed upon an external surface of the second end portion and is completely external to the envelope. The sleeve defines a cavity configured to removably receive the envelope. The first electrical contact is in communication with the cavity and is configured to electrically connect to the first electrode when the envelope is within the sleeve. The second electrical contact is in communication with the cavity and is configured to electrically connect to the second electrode when the envelope is within the sleeve. The first electrical contact and the second electrical contact are connectable to an electrical power supply, and the electrodes electrically energize the fluid when electrically connected to the electrical power supply.

In accordance with another embodiment of the present disclosure, there is provided a spectroscopy device, referred to as a spectral analysis apparatus, that includes a cartridge, a carousel, and a base. The cartridge includes a light transmissive envelope having a first electrode and a second electrode that are completely external to the envelope. The envelope contains a fluid operable to emit light when electrically energized. The carousel includes a plurality of sleeves including a first contact opening and a second contact opening. Each sleeve is configured to receive the cartridge. The base includes a first electrical contact and a second electrical contact and the carousel is movably supported on the base. The first electrical contact and second electrical contact are connectable to an electrical power supply. The carousel is movable relative to the base to position one of the sleeves in an active position in which the first contact opening is positioned to receive the first electrical contact and the second contact opening is positioned to receive the second electrical contact. In response to the cartridge being received by the sleeve in the active position the first electrical contact connects to the first electrode and the second electrical contact connects to the second electrode. The first electrode and the second electrode electrically energize the fluid when electrically connected to a corresponding electrical contact.

In accordance with another embodiment of the present disclosure, there is provided a spectroscopy device, referred to as a spectral analysis apparatus, that includes a cartridge, a carriage, a base unit, a first electrical contact, and a second electrical contact. The cartridge includes a light transmissive envelope having a first electrode and a second electrode. The first and second electrodes are completely external to the envelope. The envelope contains a fluid operable to emit light when electrically energized. The carriage defines a cavity, and the carriage is configured to removably receive the cartridge within the cavity. The base unit includes a guide structure, and the carriage is movable relative to the base unit about the guide structure. A first electrical contact within the cavity is configured to electrically connect to the first electrode when the cartridge is within the cavity. A second electrical contact within the cavity is configured to electrically connect to the second electrode when the cartridge is within the cavity. The first electrical contact and the second electrical contact are connectable to an electrical power supply. The electrodes electrically energize the fluid when electrically connected to the electrical power supply.

In accordance with another embodiment of the present disclosure, there is provided a spectroscopy device, referred to as a spectral analysis apparatus, that includes a cartridge, a receiver, a first and second electrical contact, a signaler, and a detector. The cartridge includes a light transmissive envelope having a first electrode and a second electrode that are completely external to the envelope. The envelope contains a fluid operable to emit light when electrically energized. The receiver defines a cavity that is configured to removably receive the cartridge within the cavity. The first electrical contact is within the cavity and is configured to electrically connect to the first electrode when the cartridge is within the cavity. The second electrical contact is within the cavity and is configured to electrically connect to the second electrode when the cartridge is within the cavity. The signaler is associated with one of the cartridge and the receiver. The detector is associated with the other of the cartridge and the receiver, the detector is configured to detect the signaler. The first electrical contact and the second electrical contact are connectable to an electrical power supply. The detector detects the signaler only in response to the cartridge being received completely by the cavity. The detector enables connecting of the electrical power supply to the first electrical contact and the second electrical contact in response to detecting the signaler. The detector prevents connecting of the electrical power supply to the first electrical contact and the second electrical contact in response to not detecting the signaler. The electrodes electrically energize the fluid when electrically connected to the electrical power supply.

In accordance with another embodiment of the present disclosure, there is provided a fluid filled apparatus for use with a spectral analysis device. The fluid filled apparatus includes an envelope, a first electrode, and a second electrode. The envelope is defined entirely by a light transmissive member and contains a fluid operable to emit light when electrically energized. The first electrode is disposed upon an external surface of a first portion of the envelope and is completely external to the envelope. The second electrode is disposed upon an external surface of a second portion of the envelope and is completely external to the envelope.

In accordance with another embodiment of the present disclosure, there is provided a fluid filled apparatus for use with a spectral analysis device. The fluid filled apparatus includes an envelope, a first electrode, and a second electrode. The envelope is defined entirely by a light transmissive member and the envelope has a first end portion fluidly coupled to a second end portion with a capillary portion. The envelope contains a fluid operable to emit light when electrically energized. The first electrode is positioned entirely within the first end portion of the envelope. The second electrode is positioned entirely within the second end portion of the envelope.

BRIEF DESCRIPTION OF THE FIGURES

Features of the present invention will become apparent to those skilled in the art from the following description with reference to the figures.

FIG. 11B is a perspective view of the carousel of the power unit of FIG. 1, the carousel includes numerous sleeves.

DETAILED DESCRIPTION

For the purpose of promoting an understanding of the principles of the device described herein, reference will now be made to the embodiments illustrated in the figures and described in the following written specification. It is understood that no limitation to the scope of the device is thereby intended. It is further understood that the device includes any alterations and modifications to the illustrated embodiments and includes further applications of the principles of the device as would normally occur to one skilled in the art to which this device pertains.

Figure 1:
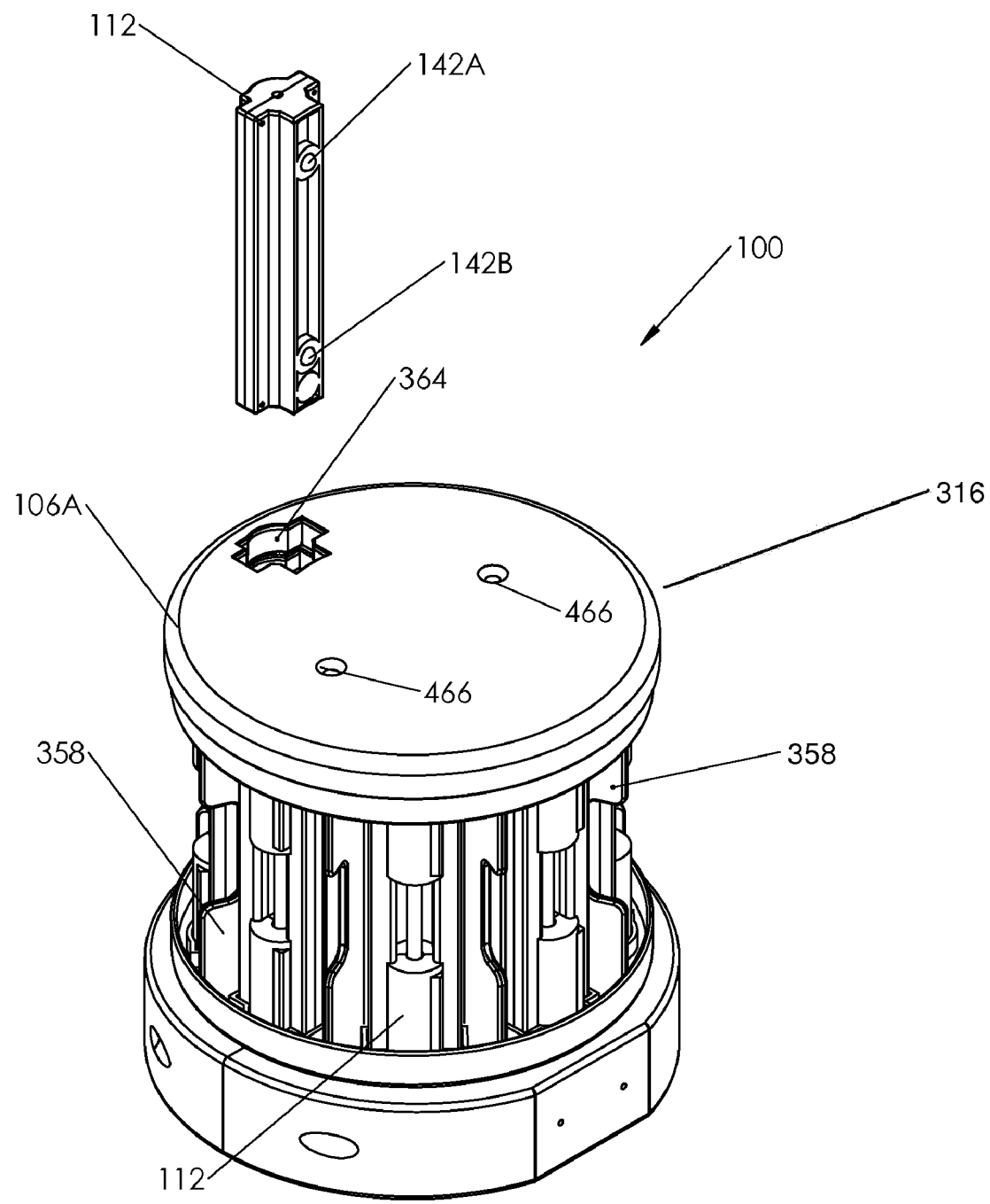
FIG. 1 is a perspective view of a spectral analysis apparatus, according to the present disclosure, the spectral analysis apparatus includes a power unit and a cartridge.
Figure 2:
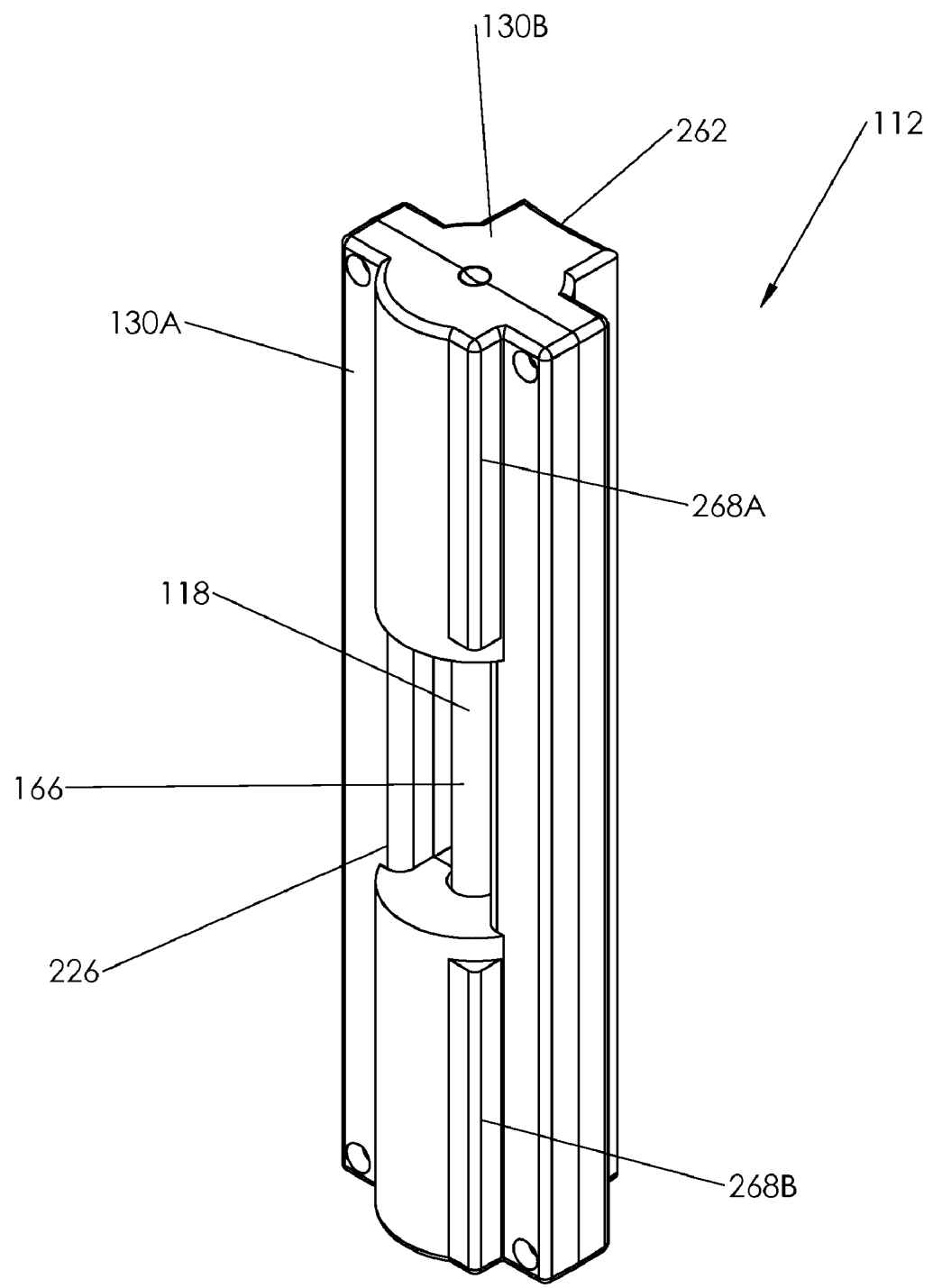
FIG. 2 is a perspective view of the cartridge of FIG. 1, the cartridge including a fluid filled envelope.

A spectral analysis apparatus 100 is shown in FIG. 1. The spectral analysis apparatus 100 includes a power unit 106A and a cartridge 112 (shown in detail in FIG. 2). A source of electrical energy 332 (FIG. 10B), which is mounted to the power unit 106A, may be electrically connected to the cartridge 112 in response to the cartridge being received within a sleeve 358 (shown in detail in FIG. 12) of the power unit 106A. The cartridge 112 emits light in response to being connected to the source of electrical energy 332. The cartridge 112 passes through an aperture 364 to be received within the sleeve 358.

Figure 3:
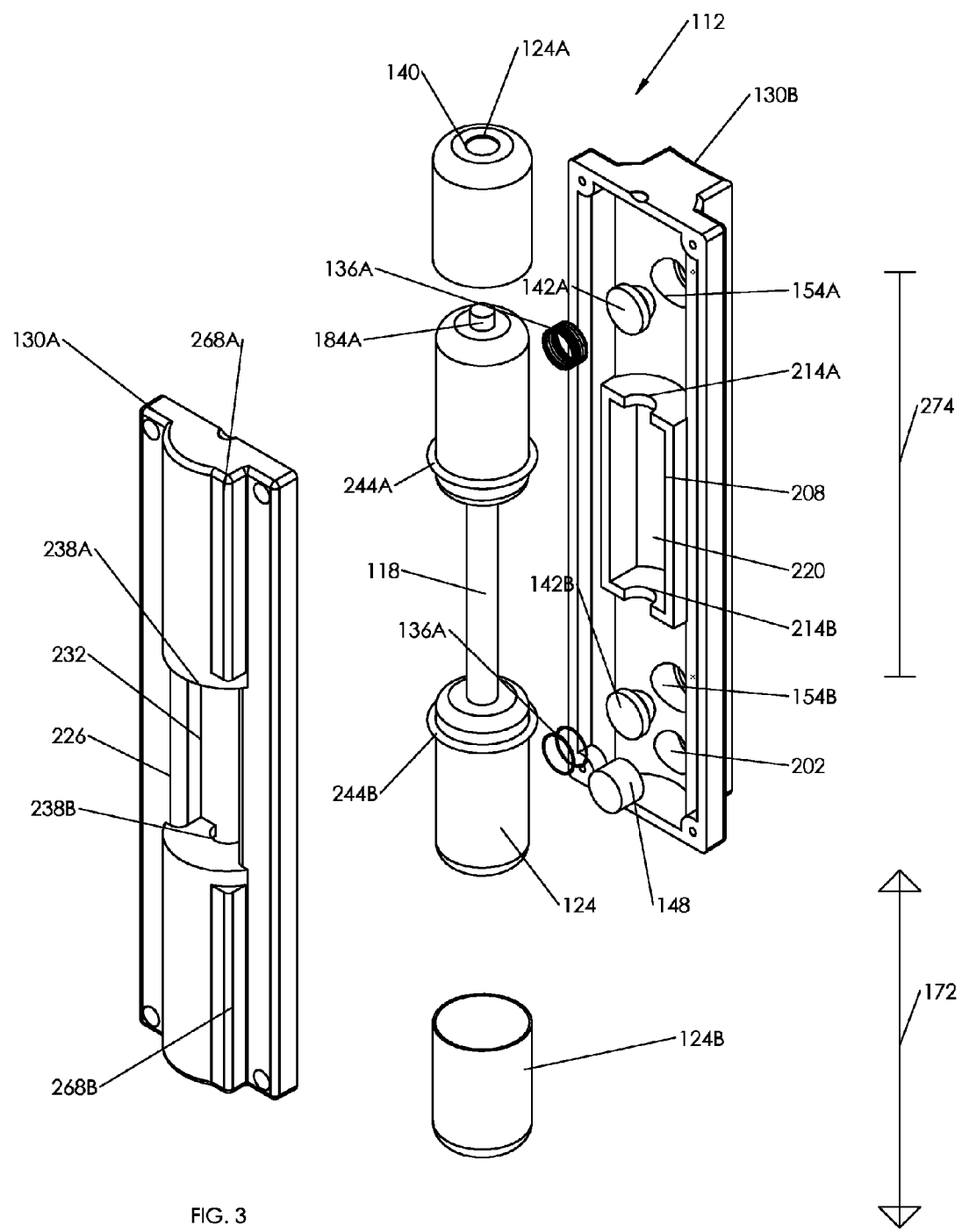
FIG. 3 is an exploded perspective view of the cartridge of FIG. 2.

As shown in FIG. 3, the cartridge includes an envelope 118; electrodes 124A, 124B; a housing 130A, 130B; springs 136A, 136B; contacts 142A, 142B; and a signaler 148. Each electrode 124A, 124B is connected to an end portion of the envelope 118. The contacts 142A, 142B are movably seated in openings 154A, 154B in the housing 130B. The springs 136A, 136B are positioned to contact the electrodes 124A, 124B and the contacts 142A, 142B, and are operable to push the contacts outward through the openings 154A, 154B. The signaler 148 is received by an opening 202 in the housing 130B.

Figure 4:
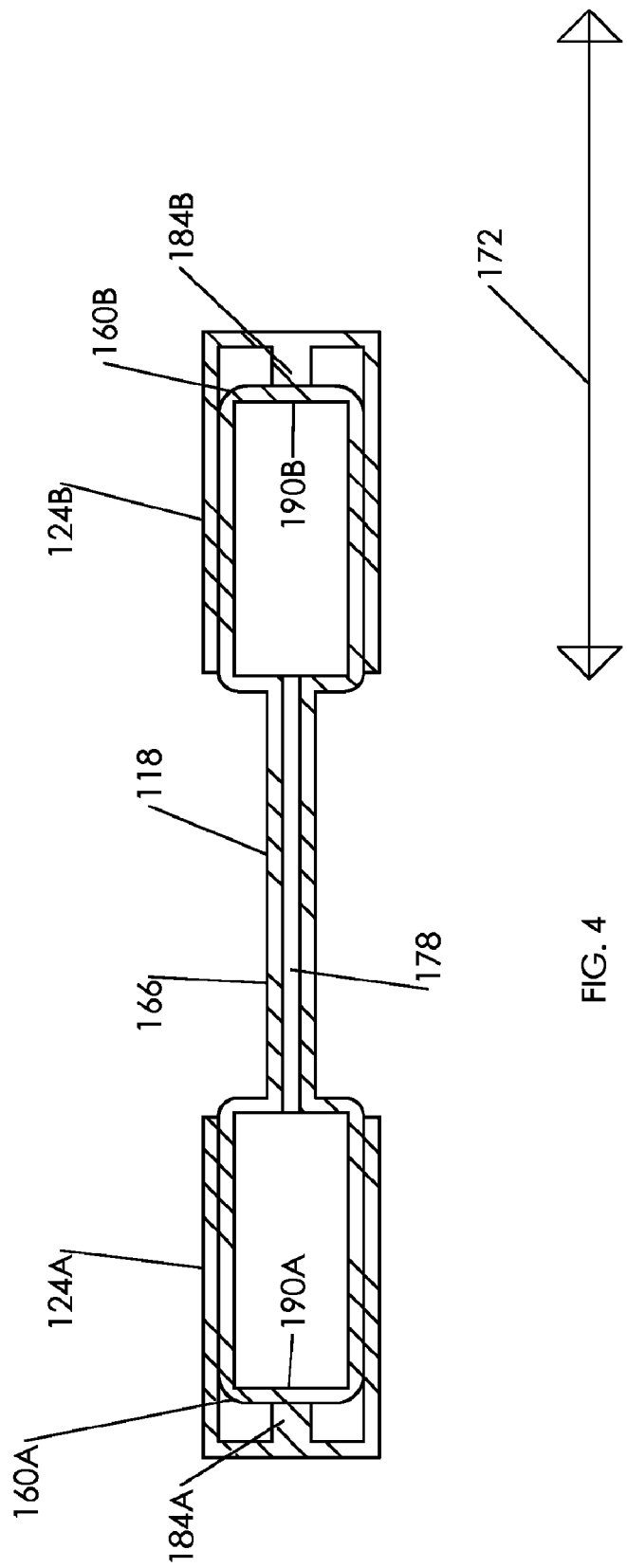
FIG. 4 is a cross sectional view of the envelope of FIG. 2, the envelope including two completely external electrodes and two sub electrodes.

A cross sectional view of the envelope 118 and the electrodes 124A, 124B is depicted in FIG. 4. The envelope 118 includes bulbs 160A, 160B separated by a capillary portion 166 along a longitudinal axis 172 of the envelope 118. The electrode 124A surrounds the bulb 160A, while the electrode 124B surrounds the bulb 160B. Sub electrodes 184A, 184B are positioned between a respective bulb 160A, 160B and a respective electrode 124A, 124B.

The envelope 118 defines a cavity 178 extending from the bulb 160A, through the capillary portion 166, and to the bulb 160B, which contains a fluid or vapor configured to be energized by the power unit 106A. The fluid is usually maintained within the envelope 118 in a gaseous phase; however, the envelope 118 is also suited to contain matter in the liquid and solid phases. The fluid may be maintained in the envelope 118 above or below the atmospheric pressure; however, it is most common to maintain the fluid at a pressure of approximately 1 to 10 Torr. Exemplary fluids that may be contained within the envelope 118 include, but are not limited to, hydrogen, helium, neon, carbon dioxide, argon, and other fluids, including fluids that are frequently studied in an educational environment. The bulbs 160A, 160B, which may also be referred to as reservoirs, provide additional volume to the cavity 178 to increase the amount of fluid that may be contained by the envelope 118, thereby extending the operating lifespan of the envelope.

The envelope 118 is formed of a light transmissive material. Exemplary materials include, but are not limited to, translucent and transparent plastics and glasses. The envelope 118 is completely sealed around the cavity 178 so that no air can be drawn into the cavity 178 (even with the fluid being maintained below the atmospheric pressure), and no fluid can escape from the cavity 178 (in response to the fluid being maintained above the atmospheric pressure). To this end, the envelope 118 is hermetically sealed with only a glass-to-glass sealing (for a glass material envelope).

Figure 5:
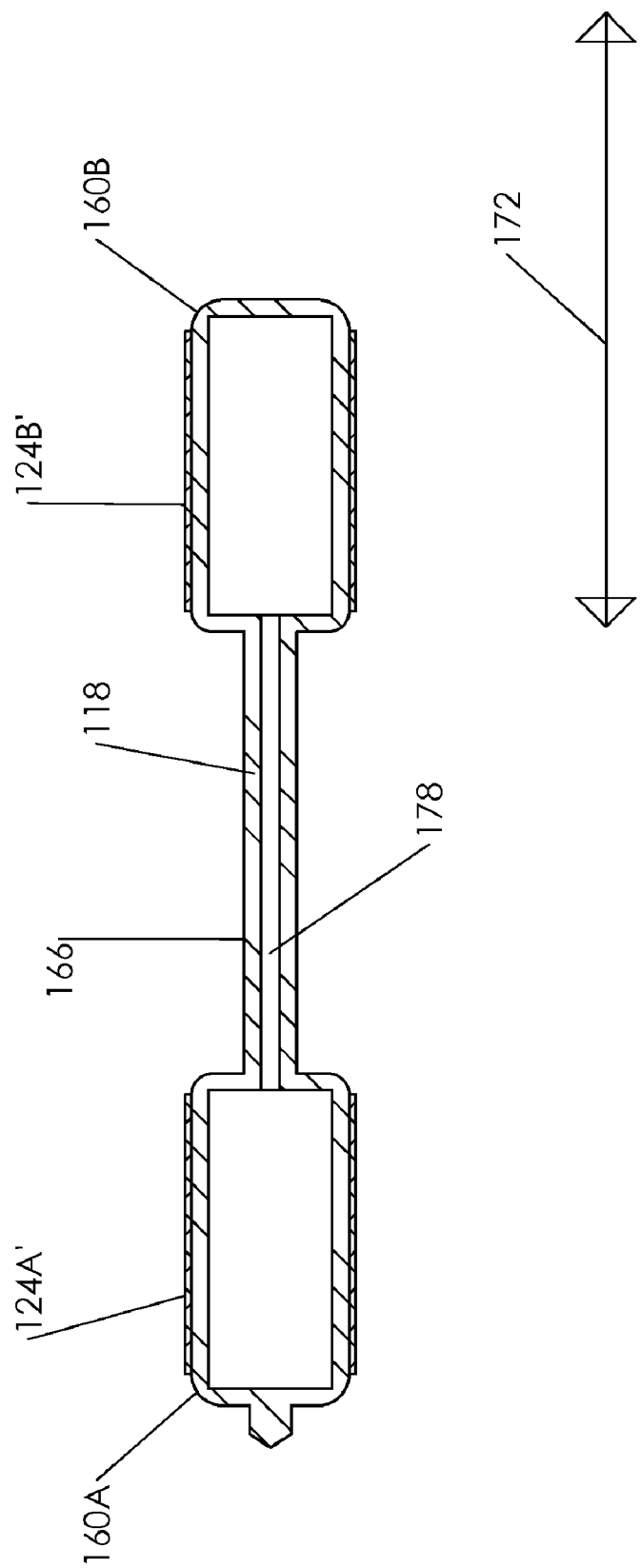
FIG. 5 is a cross sectional view of the envelope of FIG. 2, the envelope including two completely external electrodes.
Figure 6:
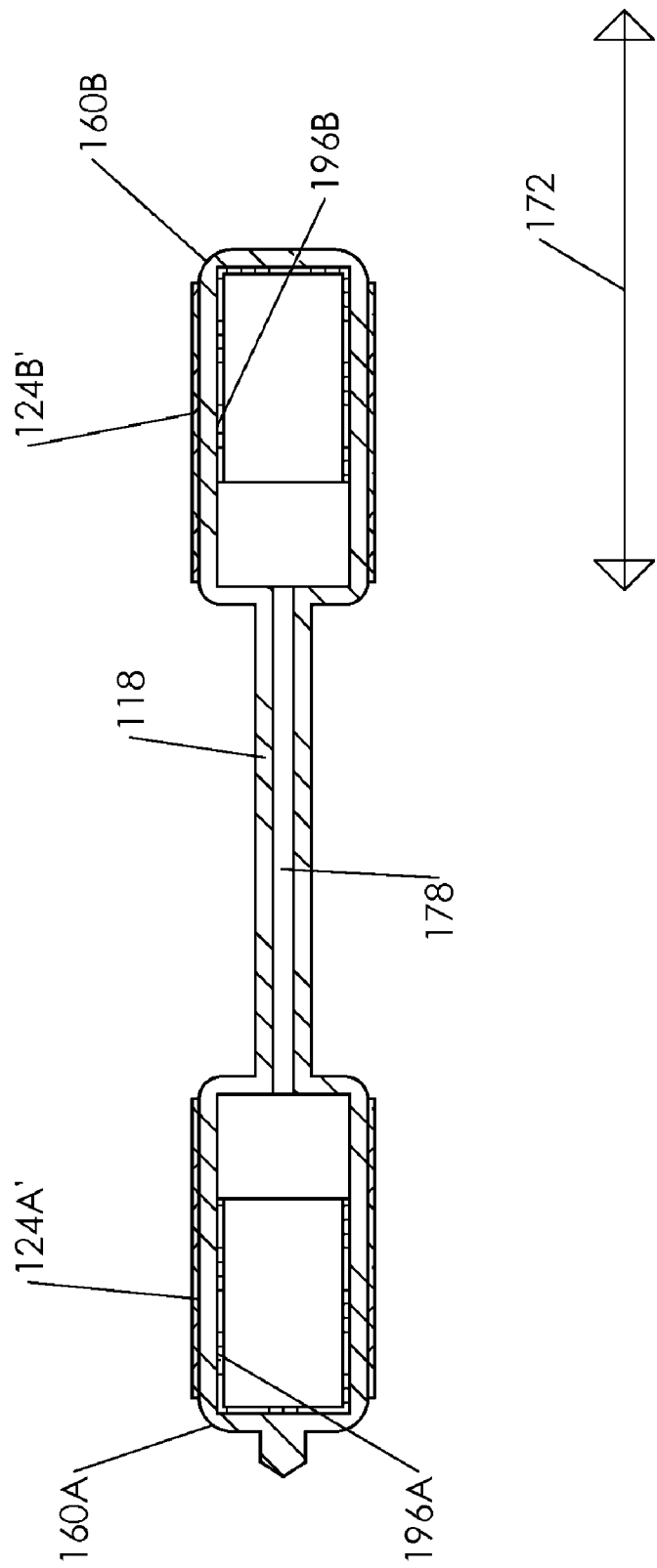
FIG. 6 is a cross sectional view of the envelope of FIG. 2, the envelope including two completely external electrodes and two completely internal electrodes.

As shown in FIGS. 4-6, various embodiments of the electrodes 124A, 124B, 124A', 124B', which are completely external to the cavity 178, are connected to the bulbs 160A, 160B of the envelope 118. The electrodes 124A, 124B, 124A', 124B' are a conductive material such as steel, aluminum, or other metals or metallic alloys. As shown in FIG. 4, the electrodes 124A, 124B are metal caps that at least partially encapsulate the exterior of the bulbs 160A, 160B. The sub electrodes 184A, 184B, which are also formed of a conductive material, are interposed between an end wall 190A, 190B of the envelope 118 and the electrodes 124A, 124B. The sub electrodes 184A, 184B, which are electrically connected to the electrodes 124A, 124B, focus the electrical energy supplied by the electrode 124A, 124B at a particular region of the end wall 190A, 190B. The electrodes 124A, 124B may include an opening 140, as shown in FIG. 3, having a width larger than a width of the sub electrodes 184A, 184B, such that the sub electrodes may extend through the electrodes 124A, 124B.

In the embodiment of FIGS. 5 and 6, the electrodes 124A', 124B' are rectangular strips that are wrapped around at least a portion of the exterior of the bulbs 160A, 160B. For example, the electrodes 124A', 124B' may be a section of conductive tape. In FIGS. 4-6, the bulbs 160A, 160B have a relatively flat exterior surface to provide a large contact zone for the electrodes 124A, 124B. An adhesive may be used to couple the electrodes 124A', 124B' to the bulbs 160A, 160B. The electrodes 124A', 124B' are thus positioned to connect electrical energy to the fluid within the cavity 178, and in particular, the electrodes 124A', 124B' induce a current through the fluid.

Figure 7:
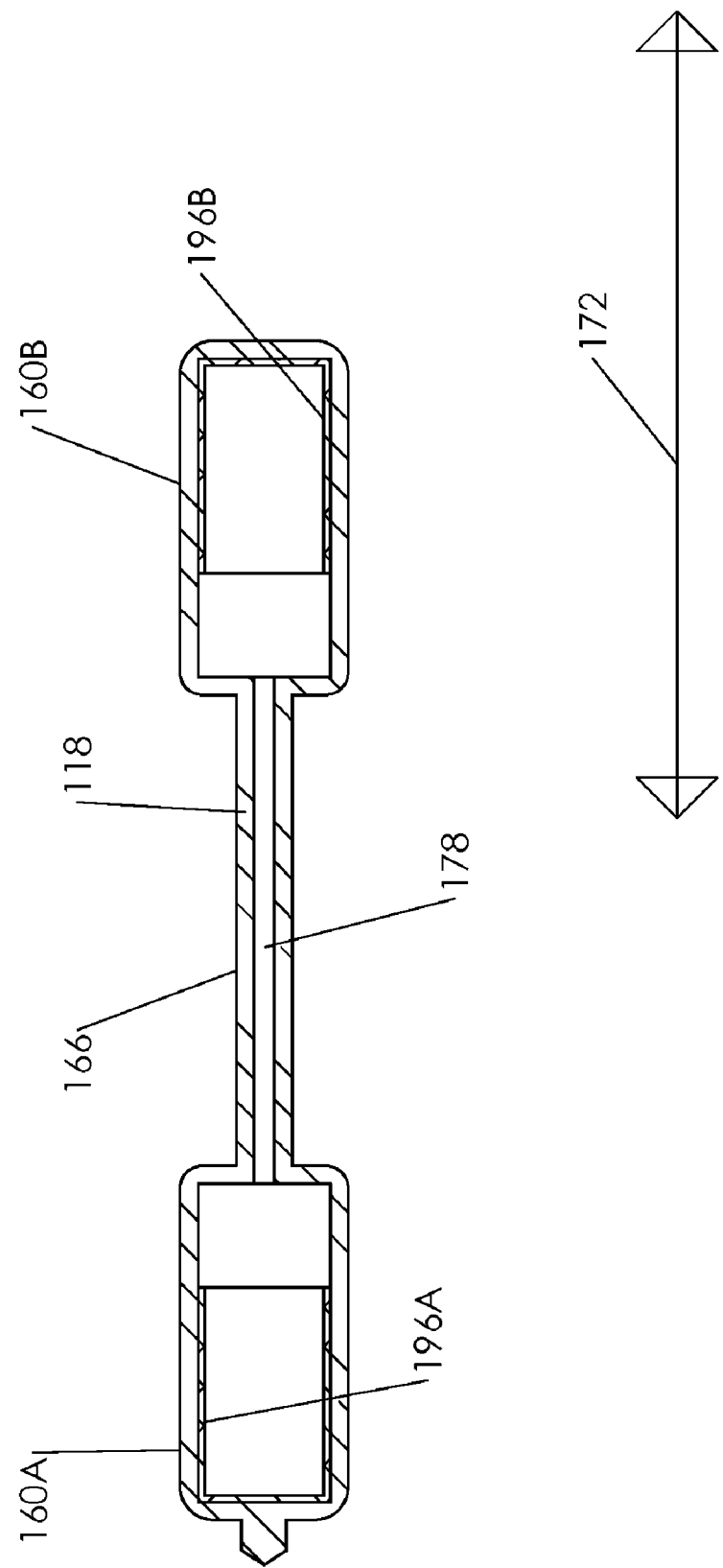
FIG. 7 is a cross sectional view of the envelope of FIG. 2, the envelope including two completely internal electrodes.

As shown in FIGS. 6 and 7, the envelope 118 may also include electrodes 196A, 196B that are completely internal to the cavity 178. The internal electrodes 196A, 196B may be the same material as the external electrodes 124A, 124B. The internal electrodes 196A, 196B are affixed to the interior surface of the bulbs 160A, 160B within the cavity 178. An envelope 118 may include any combination of the electrodes 124A, 124B, 124A', 124B', 184A, 184B, 196A, 196B. For example, as shown in FIG. 6, the envelope 118 includes the electrodes 124A', 124B' and the electrodes 196A, 196B. In such an embodiment, the electrodes 124A', 124B' transmit electrical energy to the electrodes 196A, 196B, which then energize the fluid within the cavity 178. As shown in FIG. 7, the envelope 118 includes only the electrodes 196A, 196B so that electrical energy is transmitted from the contacts 352A, 352B (FIG. 10A) of the power unit 106A to the electrodes 196A, 196B, which then energize the fluid within the cavity 178.

The envelope 118 described above has a lifespan longer than traditional spectrum tubes. The glass-to-wire seal of traditional envelopes eventually expires as a result of, among other reasons, relative motion between the wire and the envelope that occurs when the envelope is connected to a power unit. The envelope 118, according to the present disclosure, does not suffer from this weakness, because in each embodiment the cavity 178 is completely enclosed by the material of the envelope 118. In particular, no portion of an electrode 124A, 124B, 124A', 124B', 184A, 184B, 196A, 196B, or any other element, extends from within the cavity 178 to outside the cavity 178. Instead, the electrodes 124A, 124B, 124A', 124B', 196A, 196B are either entirely internal or entirely external to the cavity 178, thereby eliminating the glass-to-wire or glass-to-electrode seal of traditional envelopes. These electrodes 124A, 124B, 124A', 124B' may induce a current in the fluid contained within the cavity 178 upon being electrically connected to a source of electrical energy by way of one or more of the following processes including, but not limited to, electromagnetic induction, capacitive coupling, and radio frequency coupling.

Embodiments of the envelope 118 including only the external electrodes 124A, 124B, 124A', 124B' may have a longer lifespan than traditional spectrum tubes with internal electrodes. Internal electrodes are often subject to a condition known in the art as "sputtering", which may result from physical and/or chemical interactions between the electrode and the fluid, which can reduce the useful lifespan of the envelope. Embodiments of the envelope 118 having only the electrodes 124A, 124B, 124A', 124B' eliminate the potential for sputtering because the fluid does not contact the electrodes; accordingly, there exists no potential for physical and/or chemical interaction between the fluid and the electrodes 124A, 124B, 124A', 124B'.

Returning to FIG. 2, the cartridge 112 includes a front housing 130A and a rear housing 130B configured to encapsulate the envelope 118 and the electrodes 124A, 124B. The housings 130A, 130B may be made from a rigid molded dielectric such as an injection molded thermoplastic material. The housing 130A, 130B is an electrical insulator, such that the electrical energy passing between the envelope 118 and the electrodes 124A, 124B is not electrically connected to the housing 130A, 130B. Fastening members (not illustrated), such as screws, couple the front housing 130A to the rear housing 130A.

As shown in FIG. 3, the rear housing 130B includes the openings 154A, 154B, a cavity 202, and a support 208. The openings 154A, 154B extend through the rear housing 130B and are configured to receive the contacts 142A, 142B. The cavity 202 may be a depression in the rear housing 130B that does not extend through the rear housing. The signaler 148 is seated in the cavity 202.

The support 208 positions the envelope 118 such that the light emitted by the fluid escapes from the front housing 130A. To this end, the support 208 includes guides 214A, 214B that each define a semicircular portion having a diameter approximately the same as an outside diameter of the capillary portion 166. The guide 214A is separated from the guide 214B along the direction 172 by approximately the length of the capillary portion 166. The support 208 also includes a wall 220 that is visible behind the capillary portion 166. The wall 220 may be a dark color, such as black, to provide contrast to the color of the light emitted by the energized fluid. The wall 220 may also include a reflective element (not illustrated) to reflect the light emitted by the energized fluid. The reflective element promotes greater light collection by a tool configured to collect the light emitted by the fluid.

The front housing 130A includes a window 226 and a support 232 having guides 238A, 238B. The window 226 exposes the capillary portion 166 such that light emitted by the fluid is visible from outside of the housing 130A, 130B. The window 226 has a length in the longitudinal direction 172 that may be approximately equal to the length of the capillary portion 116. The guides 238A, 238B function similarly to the guides 214A, 214B. The guides 214A, 214B, 238A, 238B all serve to conceal the bulbs 160A, 160B thereby preventing a user from touching the bulbs through the window 226. The cartridge 112 may include o-rings 244, which surround the bulbs 160A, 160B to stabilize the envelope 118 within the cartridge 112.

Figure 8:
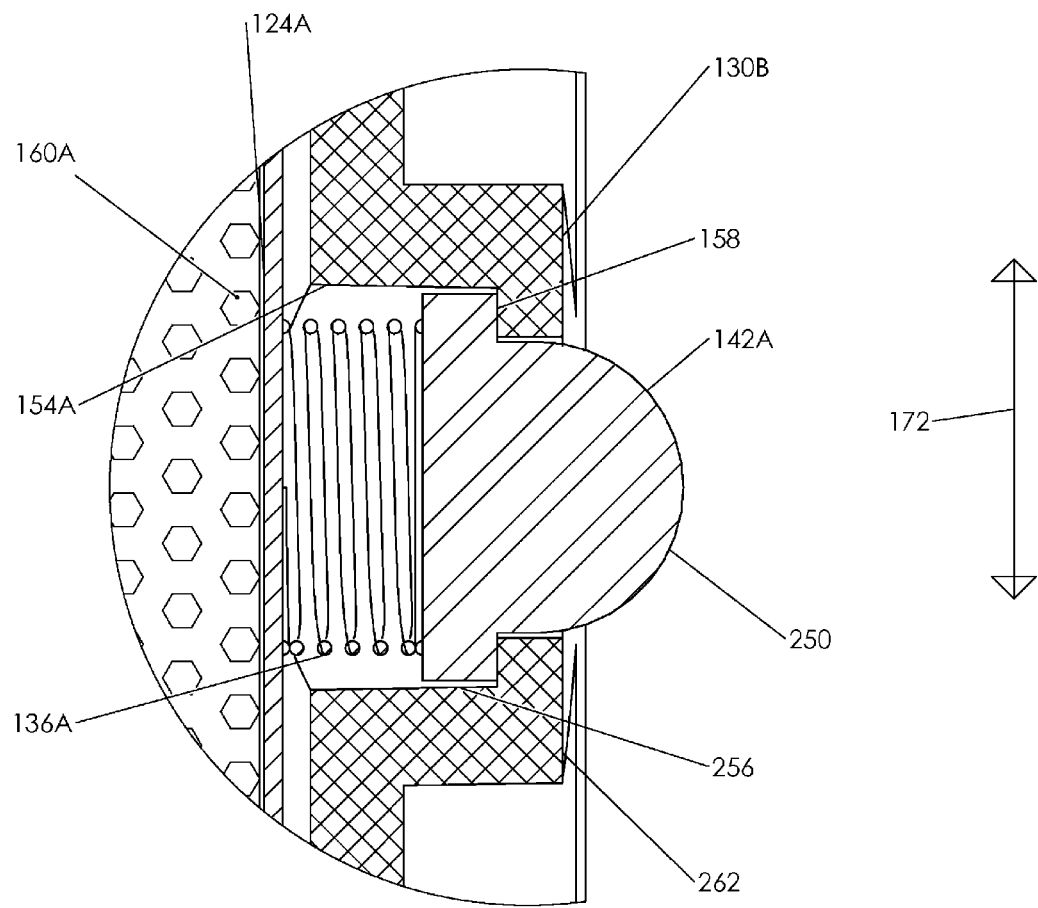
FIG. 8 is a cross sectional view of a portion of the cartridge of FIG. 2, illustrating in detail one of the electrical contacts.

As shown in FIG. 3, the contacts 142A, 142B are retained in the openings 154A, 154B. With reference to FIG. 8, the contact 142A includes a dome 250 and a base 256. The spring 136A is positioned in the opening 154A between the contact 142A and the electrode 124A. The base 256 has a width larger than a width of the dome 250 and the spring 136A biases the base 256 against a lip 158 of the opening 154A. The lip 158 contacts the base 256 to prevent the contact 142A from passing through the opening 154A, and the dome 250 extends through the opening. An object sliding against the surface 262 of the rear housing 130B in the direction 172 causes the contact 142A to move to the left against the biasing force of the spring 136A. The springs 136A, 136B are made of a conductive material to electrically connect the contacts 142A, 142B to the electrodes 124A, 124B. The contacts 142A, 142B are separated by the distance 274, which is related to the bulb-to-bulb distance of the envelope 118.

Figure 9:
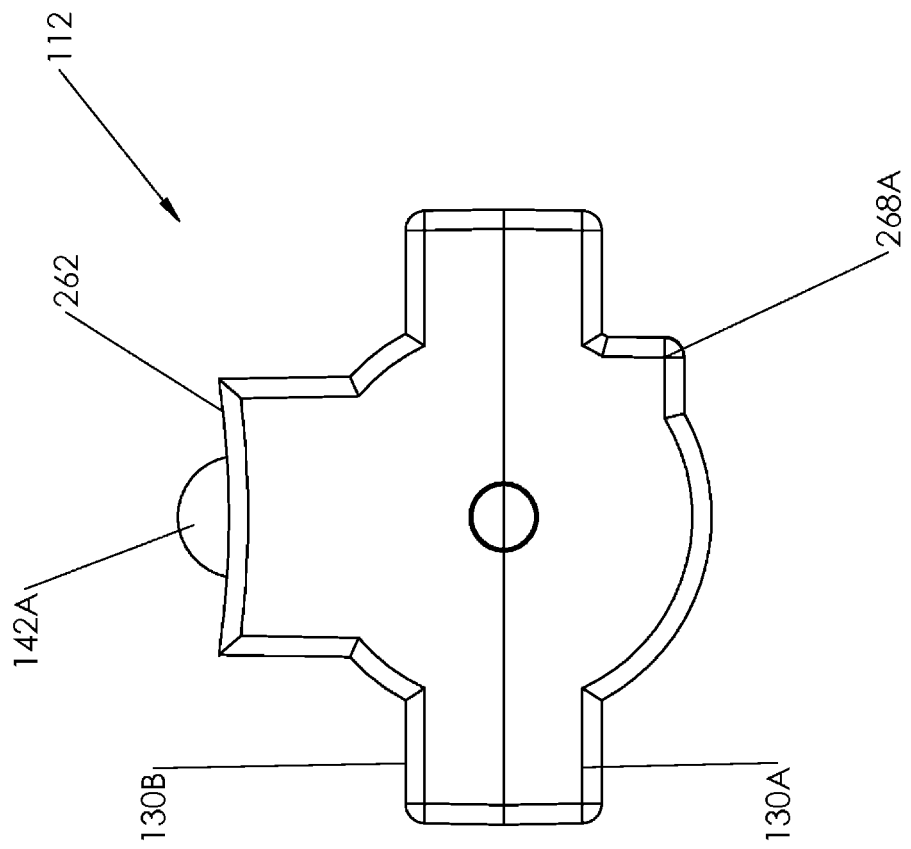
FIG. 9 is a top view of the cartridge of FIG. 2.

As shown in FIGS. 3 and 9, the housing 130A, 130B has an irregular external periphery, which includes a protuberance 268A and a protuberance 268B (FIG. 3 only). The protuberance 268A is aligned with the protuberance 268B in the longitudinal direction 172. As described more fully below, the protuberances 268A, 268B ensure that the power unit 106A receives the cartridge 112 in only one unique orientation.

The housing 130A, 130B of the cartridge 112 provides several advantages over traditional spectrum tubes, which lack a housing. First, the housing 130A, 130B prevents users from directly handling the envelope 118. Second, the housing 130A, 130B protects the envelope 118 from breakage, should a user drop the cartridge 112. Third, if an extreme physical shock were to break the envelope 118, the housing 130A, 130B contains most of the envelope material. Fourth, the protective housing 130A, 130B enables the cartridge 112 to be stacked or piled on other cartridges 112 without damaging the envelope 118 contained within each cartridge 112. Fifth, the housing 130A, 130B, may be easily labeled without affecting the performance of the envelope 118. Furthermore, the cartridge 112 enables an envelope 118 to be removed from a power unit 106A, 106B (FIG. 13A) of the apparatus 100 without requiring a user to directly contact the envelope 118.

Figure 10A:
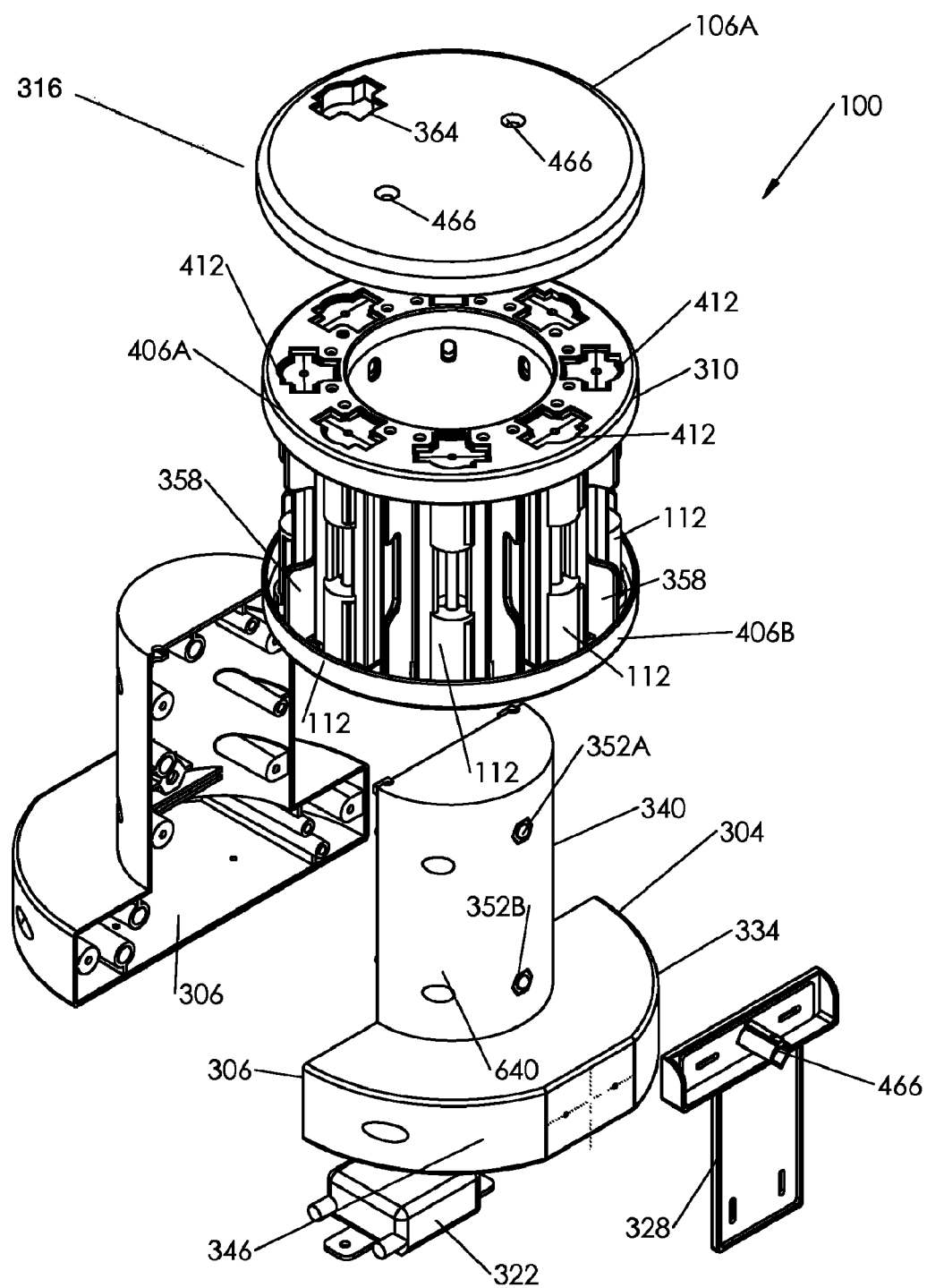
FIG. 10A is an exploded perspective view of the power unit of FIG. 1, the power unit being configured to receive the cartridge within one of numerous sleeves.
Figure 10B:
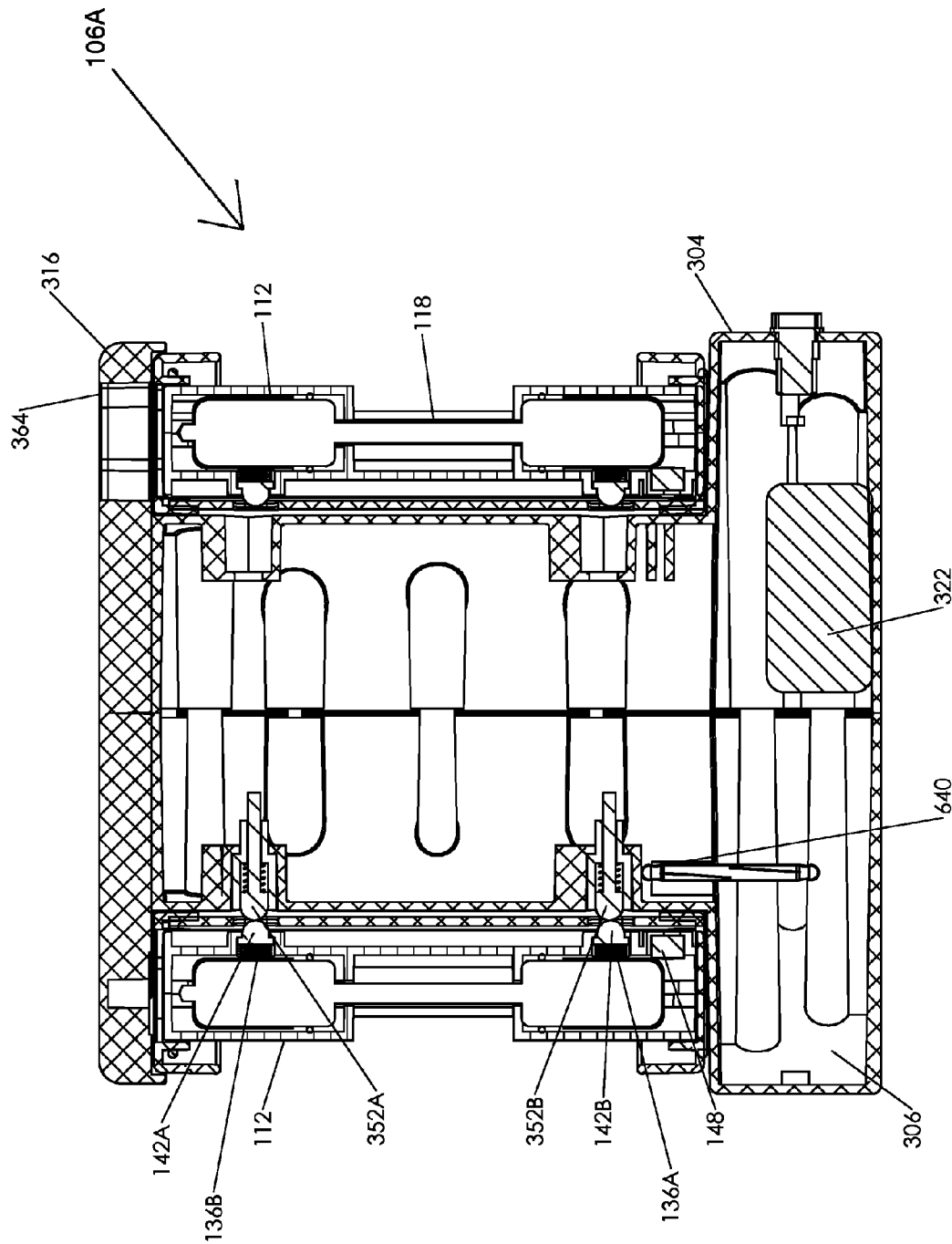
FIG. 10B is a cross sectional view of the power unit of FIG. 1.

The power unit 106A of the apparatus 100 is illustrated in FIGS. 10A and 10B. The power unit 106A includes a base 304, a carousel 310, a cap 316, a power supply 322, and a tool holder 328. The base includes a foot 334, a post 340, a switch 346, contacts 352, and a switch 640. The carousel 310 (shown isolated in FIG. 11B) is positioned to rotate about the post 340 and includes numerous sleeves 358 (shown isolated in FIG. 12), each configured to receive a cartridge 112. The cap 316 is connected to the top of the post 340 to limit the movement of the carousel 310 relative to the post 340 in the longitudinal direction 172. The power unit 106A receives cartridges 112 through an aperture 364 in the cap 316.

The base 304 defines an internal cavity 306 configured to contain the power supply 322, as shown in FIG. 10B. The halves of the base 304, which may be formed from an injection moldable thermoplastic, depicted in FIG. 10A may be fastened together once the components are mounted inside. As illustrated in FIG. 10A, the post 340 is integral with the foot 334; alternatively, the post 340 may be separate from, but connected to the foot 334.

Figure 11A:
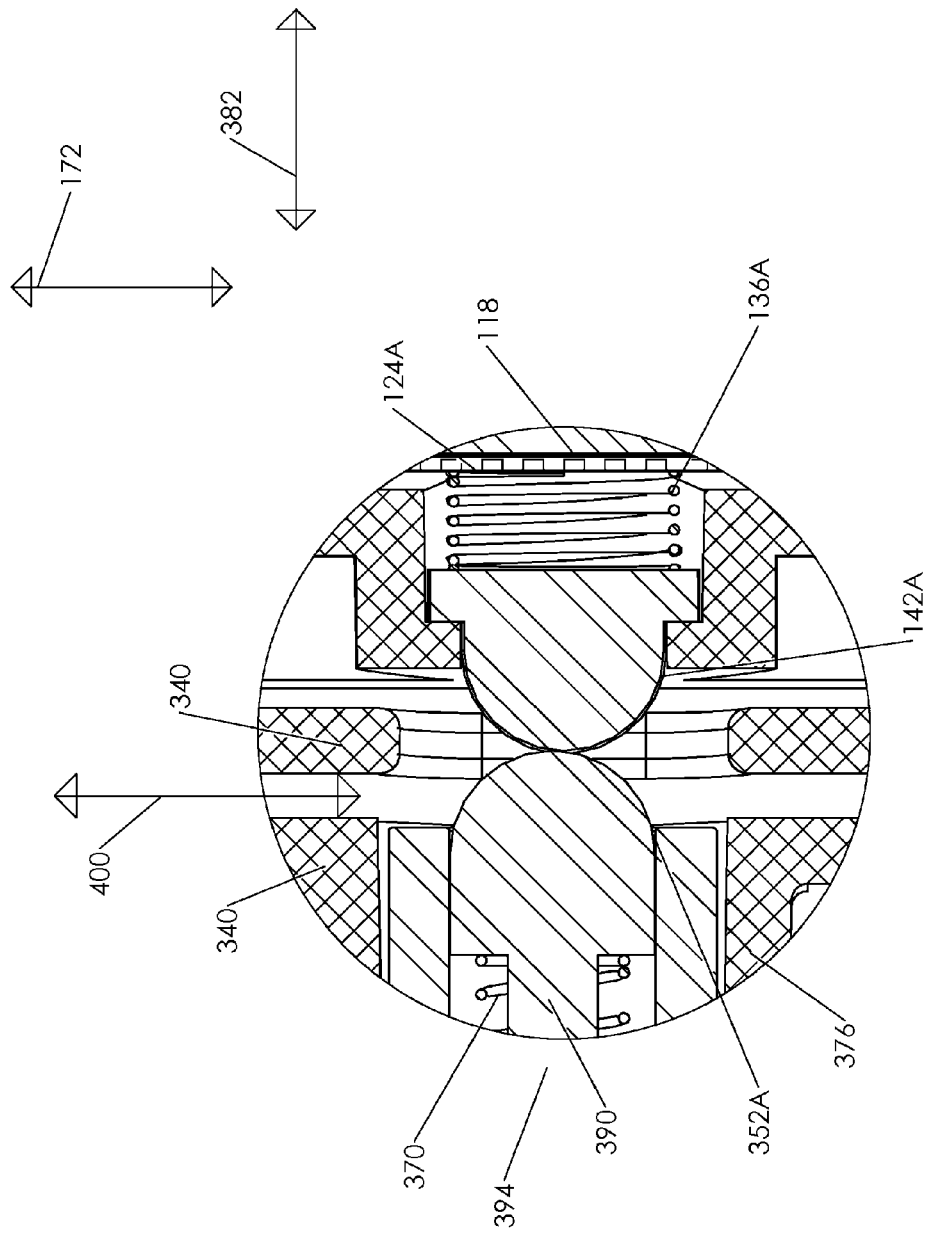
FIG. 11A is a cross sectional view of a portion of the power unit of FIG. 1 and a portion of the cartridge received by the power unit.

As shown in FIGS. 10B and 11A, the contact 352A and a spring 370 are retained within a contact unit 376 of the post 340. The contact 352A is structurally similar to the contacts 142A, 142B, except that the contact 352A may include an extension shaft 390. The contact 352A is movable in a direction 382 within the contact unit 376. The contact unit 376 defines a lip 388, which retains the contact 352A within the unit 376. The contact 352A has a domed surface such that a force exerted upon the contact 352A in the direction 172, or in a direction into or out of the page of FIG. 11A, causes the contact 352A to retract within the contact unit 376 against the biasing force of the spring 370. The spring 370 electrically connects the contact 352A to the contact unit 376, which is electrically connected to the power supply 322 via the electrical connection 394. The spring 370 and the contact unit 376 are thus made of a conductive material such as metal. The contact 352B is retained within a similar contact unit.

The contacts 352A, 352B protrude from the post 340 in response to the biasing force of the springs 370. As shown in FIG. 11A, a plane 400 defined by the post 340 intersects the contact 352A. The contact 352A is separated from the contact 352B by a distance equal to the separation between the contact 142A and the contact 142A, e.g. the distance 274.

As shown in FIG. 10B, the switch 640 is connected to a rear side of the post 340 within the cavity 306. In particular, the switch 640 is positioned in the cavity 306 and just below the contact 352B. Accordingly, the switch 640 is not positioned to be contacted by a user of the power unit 106A.

As shown in FIG. 11B, the carousel 310 includes annular plates 406A, 406B and sleeves 358. The plate 406A, 406B and sleeves 358 may be formed from an injection moldable thermoplastic to define an opening having an internal diameter approximately equal to the external diameter of the post 340, such that the post 340 may extend through the plates 406A, 406B. The plate 406B is connected to a bottom side of each sleeve 358, and the plate 406A is connected to a top side of each sleeve 358. The upper plate 406A includes a plurality of apertures 412 that have a periphery that matches the periphery of the cartridge 112. The lower plate 406B includes numerous ridges 436 each having a periphery that matches the periphery of the cartridge 112.

Figure 12:
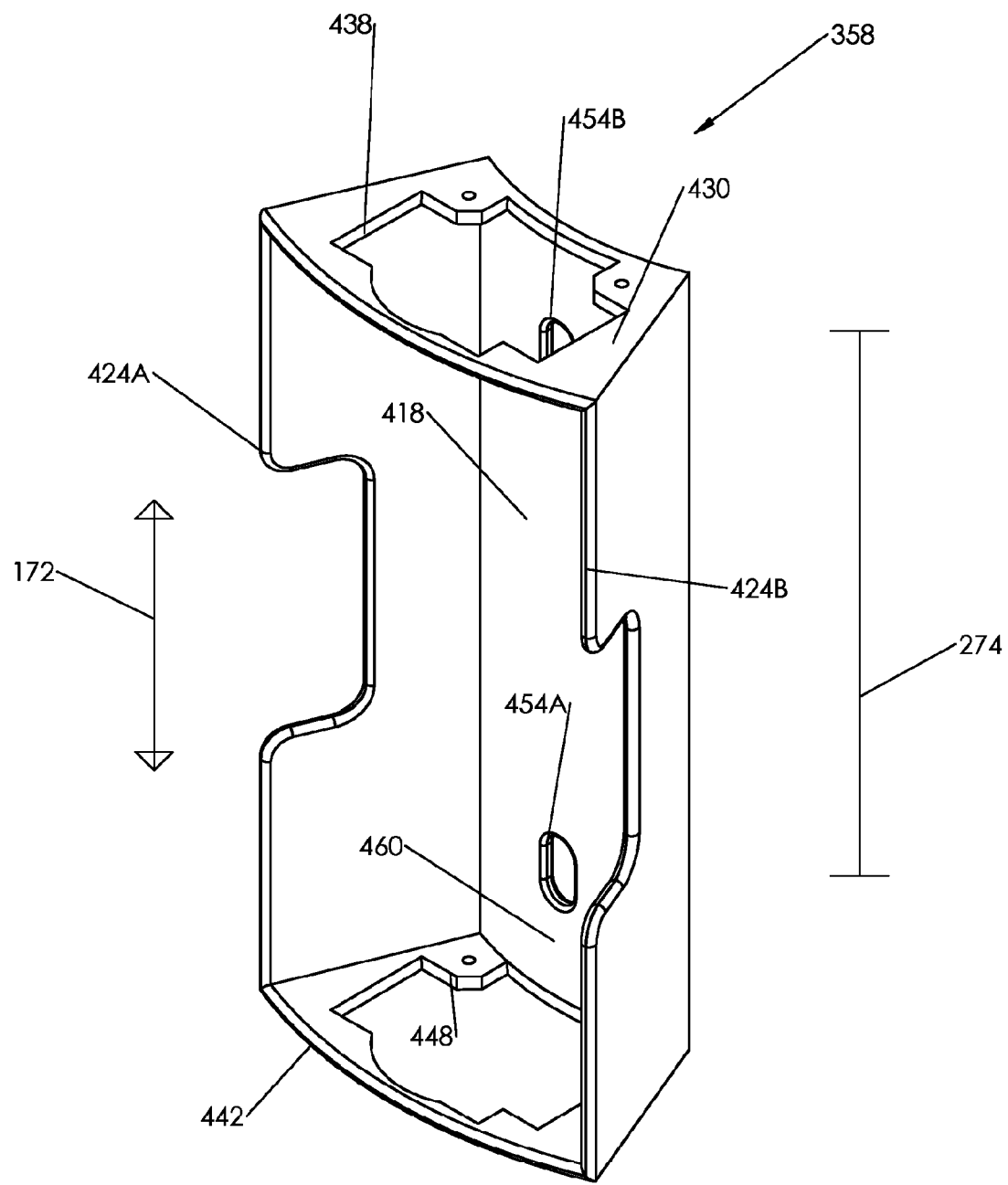
FIG. 12 is a perspective view of a sleeve of the power unit of FIG. 1.

As shown in FIG. 12, each sleeve 358 includes a rear wall 418 having openings 454A, 454B; sidewalls 424A, 424B; a bottom wall 430 having an aperture 438 and in some embodiments a top wall 442 having an aperture 448. The walls of the sleeve 358 define a cavity 460 configured to receive a cartridge 112. The rear wall 418 is positioned adjacent to the post 340, and the centers of the openings 454A, 454B are separated by the distance 274. The aperture 448 and the aperture 438 define a periphery approximately the same as the periphery of the cartridge 112. As shown in FIG. 11B, each ridge 436 in the annular plate 406B extends through a corresponding aperture 438 of each sleeve 358 when the carousel 310 is assembled. A portion of the cartridge 112 is received by the ridge 436 to prevent the cartridge 112 from moving in a direction other than up, after being received by the sleeve 358. A length of the sleeve 358 as measured in the longitudinal direction 172 is approximately equal to the length of the cartridge 112 as measured in the longitudinal direction 172. When the sleeve 358 is connected to the plate 406A, the aperture 448 is aligned with the aperture 412. As illustrated, the carousel 310 includes eight sleeves 358, although it may include any number of sleeves to carry a like number of cartridges 112.

The carousel 310 is rotatable about the post 340 to position any one of the sleeves 358 in an active position and the remaining sleeves 358 in an inactive position. The sleeve 358A in FIG. 10B is in the active position. The contacts 352A, 352B extend through the openings 454A, 454B and into the cavity 460 of the sleeve 358 in the active position. The contacts 352A, 352B are decoupled from the cavities 460, and in particular the openings 454A, 454B of each sleeve 358 in the inactive position. Additionally, the carousel 310 is rotatable about the post 340 to position all of the sleeves 358 in the inactive position.

With reference again to FIG. 1, the cap 316 is connected to the top of the post 340. The cap 316, which may be an injection moldable thermoplastic material, includes the aperture 364 and openings 466. The aperture 364, as shown in FIG. 10A, is positioned on the side of the post 340 opposite the contacts 352A, 352B, such that the aperture 438 of a sleeve 358 that is aligned with the aperture 364 is in the inactive position. In other embodiments, however, cap 316 may be connected to the top of the post 340 to align the aperture 364 with the contacts 352A, 352B, such that the aperture 438 of a sleeve 358 that is aligned with the aperture 364 is in the active position. The aperture 364 defines an opening that matches the external periphery of the cartridge 112 so that a cartridge 112 may be properly loaded into a sleeve 358 through the aperture 364.

A sleeve 358 in the active position is configured to receive the cartridge 112 oriented in the unique orientation, discussed above. The unique orientation is the only orientation in which the cartridge 112 may pass completely through the aperture 364 in the longitudinal direction 172. As shown in FIG. 9, due to the protuberances 268A, 268B, the cartridge 112 is not symmetrical when viewed in the longitudinal direction 172. Accordingly, the cartridge 112 must be oriented to align the protuberances 268A, 268B with the portion of the aperture 364 corresponding to the protuberances. In the unique orientation, the window 226 faces away from the post 340 and the contacts 142A, 142B face toward the post 340. The aperture 364 does not accept the cartridge 112 with the window 226 facing toward the post 340 and does not accept the cartridge upside down.

To place a cartridge 112 into a sleeve 358, first the carousel 310 is rotated about the post 340 until the aperture 438 of the sleeve 358 is aligned with the aperture 364. Next, the cartridge 112 is positioned in the unique orientation relative to the aperture 364 and is moved downward in the longitudinal direction 172 until the cartridge 112 passes through all of the apertures. As the cartridge 112 is moved through the aperture 364 the contacts 142A, 142B are forced to move toward the envelope 118 against the biasing force of the springs 136A, 136B. In particular, as shown in FIG. 10A, the periphery of the aperture 364 matches the periphery of the cartridge 112 excluding the contacts 142A, 142B, which retract into the housing 130B upon contacting the cap 316. The cartridge 112 is moved downward until the cartridge is received by the ridge 436. Upon being seated in the ridge 436, the cartridge 112 is received fully by the sleeve 358. The carousel 310 may rotated about the post 340 to position the cartridge 112 and sleeve 358 in the active position, in which the contacts 142A, 142B make electrical contact with the contacts 352A, 352B and the signaler 148 is positioned adjacent to the switch 640.

To remove the cartridge 112 from the sleeve 358, first the carousel 310 is rotated about the post 340 until the cartridge 112 is aligned with aperture 364. Next, the cartridge 112 is moved upward in the longitudinal direction 172 through the aperture 364.

The tool holder 328 may be connected or coupled to the foot 334 to position a tool to receive the light emitted by the energized envelope 118. The tool holder 328 includes a holder 466 configured to hold, for instance, the end of a fiber optic digital spectrometer sensor cable in the appropriate position for receiving the light emitted by the envelope 118.

Figure 13A:
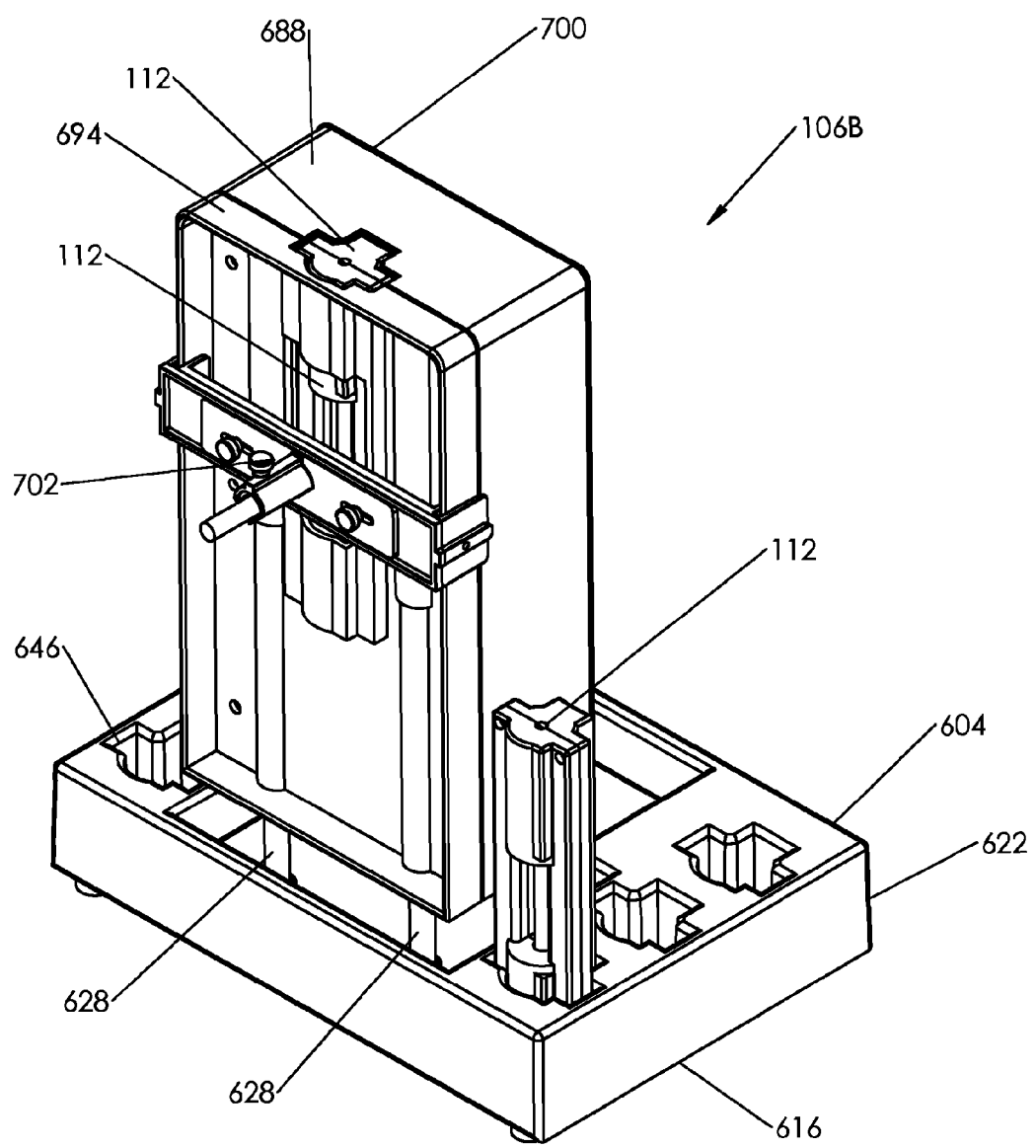
FIG. 13A is a perspective view of an alternative power unit of the spectral analysis apparatus.
Figure 13B:
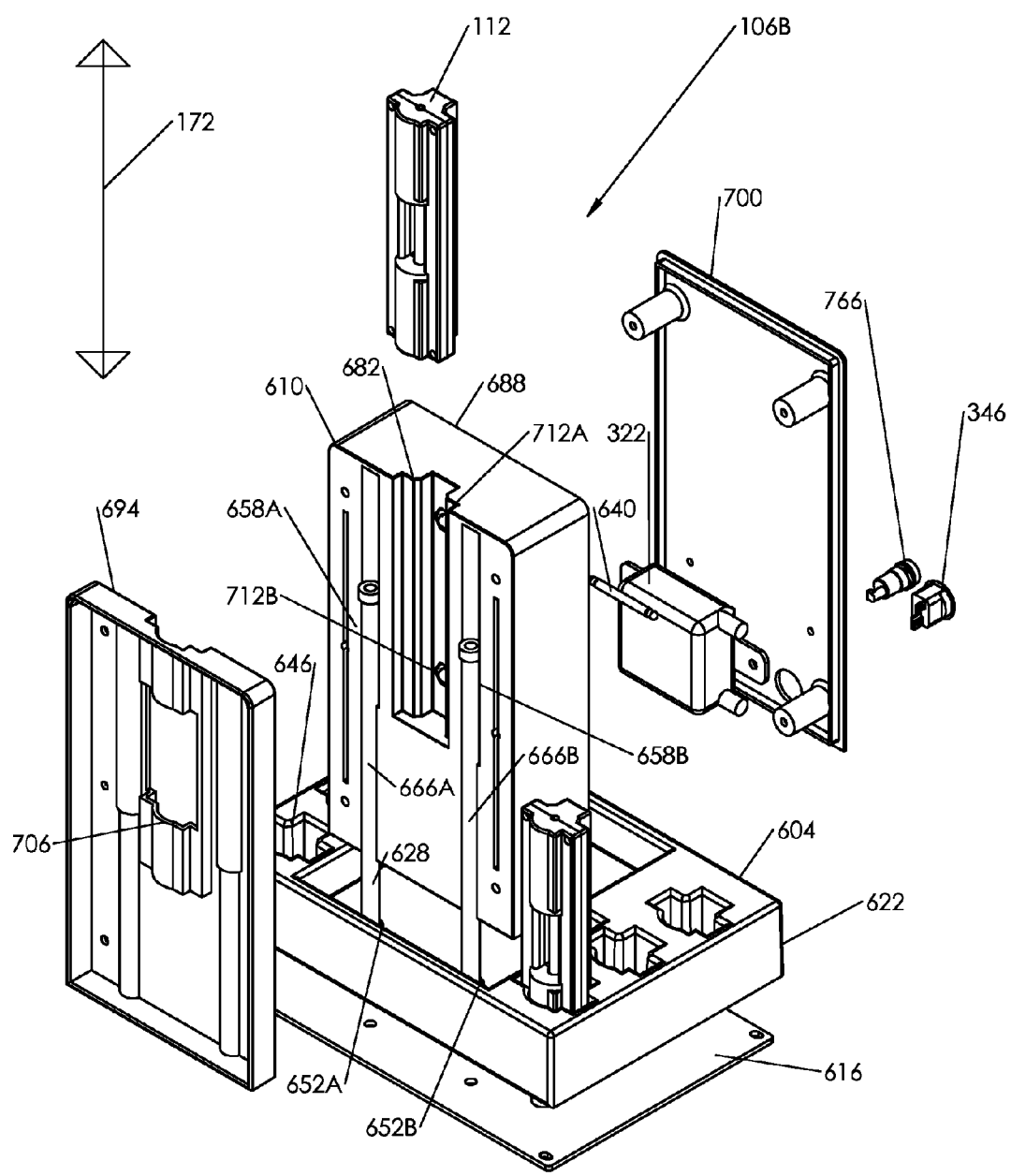
FIG. 13B is an exploded perspective view of the power unit of FIG. 13A.

A second power unit 106B is illustrated in FIGS. 13A and 13B. Instead of the power unit 106A, the apparatus 100 may include in the power unit 106B, which includes a base 604 and a carriage 610. The base 604 of the power unit 106B includes a base plate 616 connected to a footer 622 and a guide structure 628. The base plate 616 is configured to be placed on a work surface (not illustrated) and may be constructed from a rigid material such as sheet metal. The footer 622 includes numerous receptacles 646 for receiving and storing the cartridges 112. The carriage 610 includes a body 688, a front plate 694, a rear plate 700, and the power supply 322 (FIG. 13B). The carriage 610 is movable relative to the base 604 about shafts 658A, 658B of the guide structure 628. The carriage 610 defines a receiver 682 for receiving a cartridge 112. The cartridge 112 received by the receiver 682 may be electrically connected to the power supply 322 to cause the fluid within the cartridge 112 to emit light.

Receptacles 646 are provided for storing and/or organizing multiple cartridges 112. The cartridge 112 received by the receptacle 646 is not electrically connected to the power supply 322. Each receptacle 646 has a peripheral shape that matches the periphery of the cartridge 112. Accordingly, the cartridge 112 may only be inserted into the receptacle 646 in the unique orientation. As shown in the FIG. 13A, the footer 622 includes six receptacles 646. Alternatively, the footer 622 may include between zero and eighteen receptacles 646.

The guide structure 628 includes a shaft 658A and a shaft 658B. The shafts 658A, 658B are formed from a rigid material such as steel or another metal or metallic alloy. A bottom end of each shaft 658A, 658B is connected to the base plate 616 with fastening members (not illustrated). Alternatively, the shafts 658A, 658B are welded to the base plate 616. The shafts 658A, 658B extend upward in the longitudinal direction 172 through openings 652A, 652B in the footer 622. Each shaft 658A, 658B is received by the carriage 610. The guide structure 628 enables the carriage 610 to move in the longitudinal direction 172 relative to the base 604 about the shafts 658A, 658B.

Figure 14A:
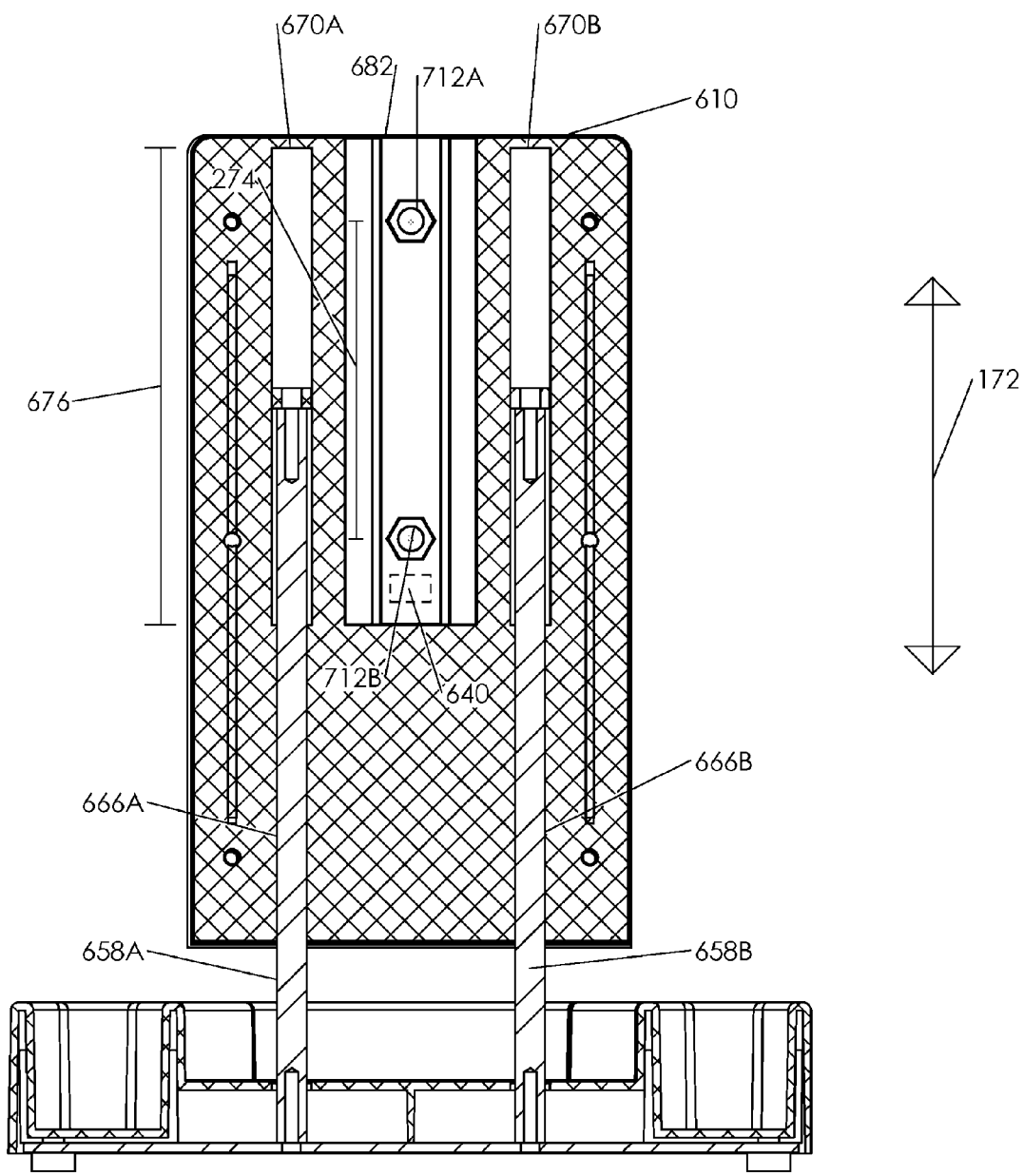
FIG. 14A is a cross sectional view of a portion of the power unit of FIG. 13A.
Figures 14B, 14C:
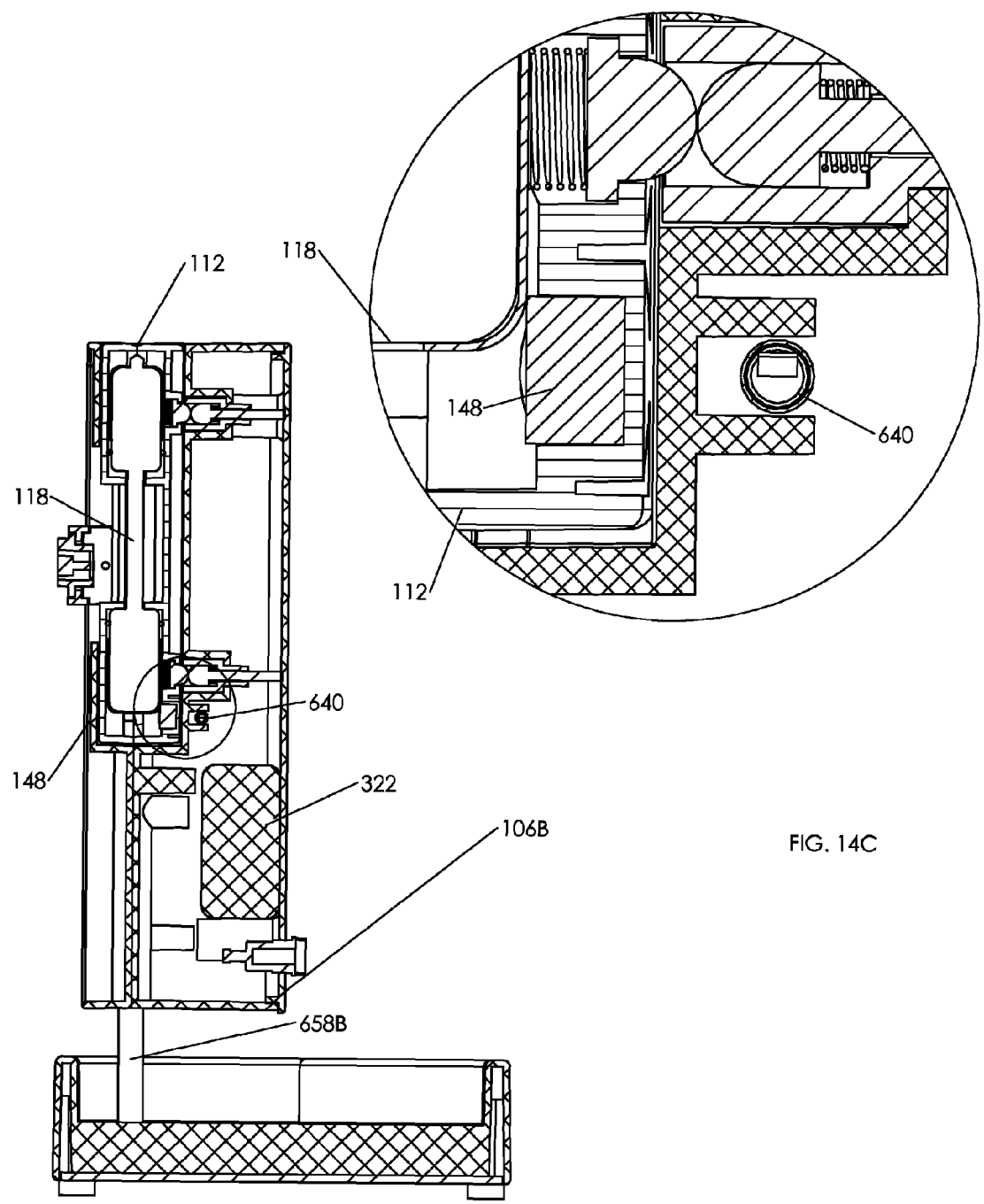
FIG. 14B is a cross sectional view of the power unit of FIG. 13A
FIG. 14C is a cross sectional view of a portion of the power unit of FIG. 13A, showing in detail a safety unit of the power unit.

As shown in FIG. 14B, the body 688 of the carriage 610 defines an internal cavity configured to house completely the power supply 322 and a switch 640 and to house partially a switch 346. The rear plate 700 is connected to the body 688 to enclose the cavity defined by the body 688. The rear plate 700 is generally imperforate. The front plate 694 is connected to a front side of the body 688. The front plate 694 and the body 688 define the receiver 682, which receives one of the cartridges 112. The front plate 694 and the body 688 also define channels 666A, 666B, and cavities 670A, 670B, both of which receive the shafts 658A, 658B of the guide structure 628.

As shown in FIG. 14A, a top end of each shaft 658A, 658B is positioned within the cavity 670A, 670B formed in the carriage 610. Each cavity 670A, 670B has a length 676 as measured in the longitudinal direction 172. The length of the cavity 670A, 670B determines the range of movement between the carriage 610 and the base 604. When the carriage 610 is in a fully lowered position, in which the carriage 610 is positioned nearest to the base 604, a top of each shaft 658A, 658B contacts or is positioned near an upper end of the cavity 670A, 670B. When the carriage 610 is in a fully raised position, in which the carriage 610 is positioned away from the base 604, the top of each shaft 658A, 658B is positioned near a lower end of the cavity 670A, 670B. Each shaft 658A, 658B may include a washer 664A, 664B or other element that is connected to the top of each shaft 658A, 658B to prevent the carriage 610 from being separated from the base 604.

A "friction fit" exists between the shafts 658A, 658B and the channels 666A, 666B, such that the guide structure 628 maintains the position of the carriage 610 relative the base 604. In particular, the weight of the carriage 610 does not cause the carriage to fall toward the base 604. Instead, friction between the carriage 610 and the shafts 658A, 658B maintains the vertical position of the carriage 610.

The carriage 610 is movable relative to the base 604 about the guide structure 628 in a vertical direction. Alternatively, the guide structure 628 may extend from the base plate 616 in a direction other than vertical, such as in a direction having a horizontal component or in the horizontal direction. Accordingly, the carriage 610 may be configured to move relative to the base 604 in a direction other than vertical.

As shown in FIG. 13B, the receiver 682 includes a window 706 and the contacts 712A, 712B. The window 706 is formed in the front plate 694 and is sized to expose the capillary portion 166 of a cartridge 112 received by the receiver 682. The contacts 712A, 712B are mounted to the carriage 610 and operate similarly to the contacts 352A, 352B. The contact 712A makes electrical contact with the contact 142A, and the contact 712B makes electrical contact with the contact 142B. The receiver 682 defines a periphery that matches the periphery defined by the cartridge 112, such that the cartridge 112 is receivable by the receiver in only the unique orientation, as defined above. As shown in FIG. 14C, the switch 640 of the carriage 610 is positioned in the cavity defined by the body 688 near the contact 712B to align with the signaler 148 of a fully received cartridge 112. Accordingly, the switch 640 is not positioned to be contacted by a user of the power unit 106B.

To place a cartridge 112 into the receiver 682, the cartridge 112 is positioned in the unique orientation relative to the periphery of the receiver 682. Next, the cartridge 112 is moved downward in the longitudinal direction 172 until an upper end of the cartridge is flush with a top surface of the carriage 610. When the cartridge 112 is received fully by the receiver 682, the contacts 142A, 142B make electrical contact with the contacts 712A, 712B, and the signaler 148 is positioned adjacent to the switch 640, as shown in FIG. 14B. The cartridge 112 is removable from the receiver 682 by moving the cartridge up in the longitudinal direction 172.

Figure 15A:
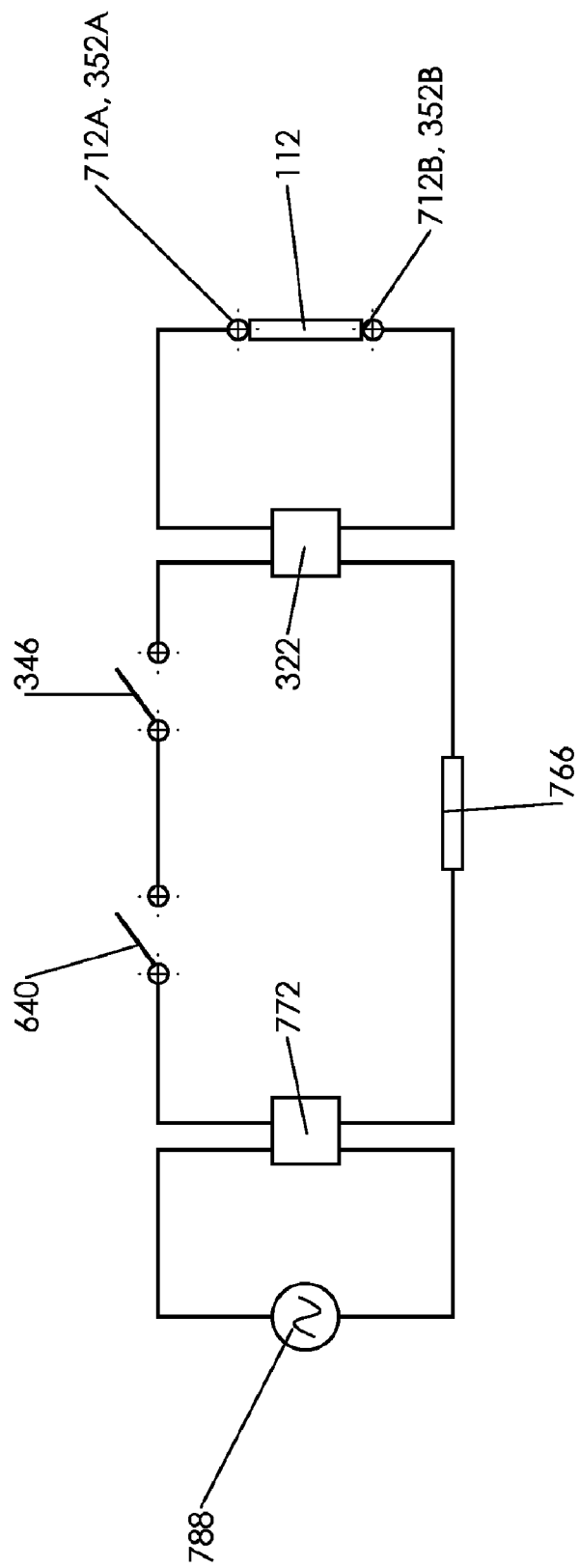
FIG. 15A is a schematic of an electrical circuit of the power unit of FIG. 1 and the power unit of FIG. 13A.
Figure 15B:
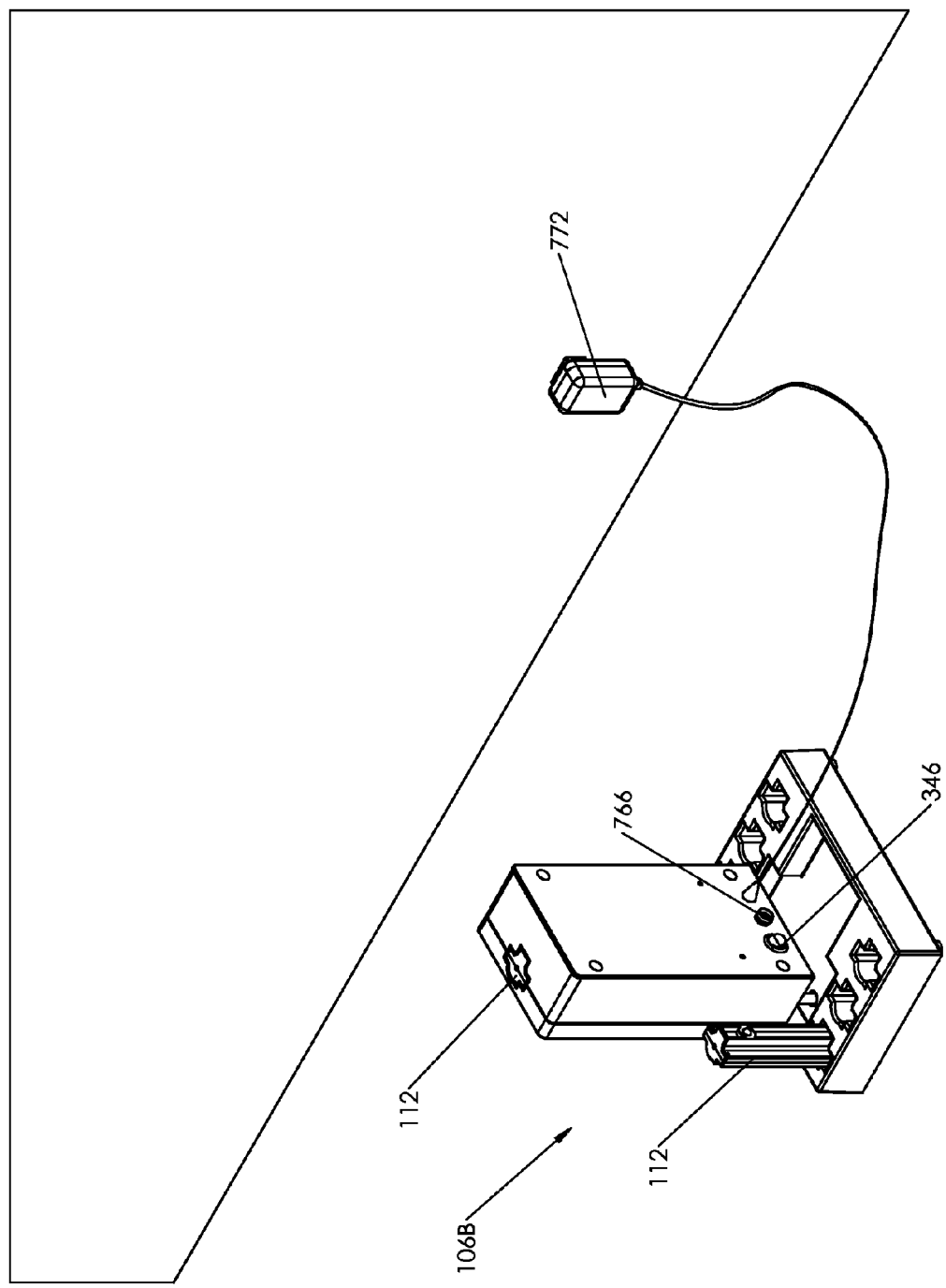
FIG. 15B is a perspective view of the power unit of FIG. 13A.
Figure 16:
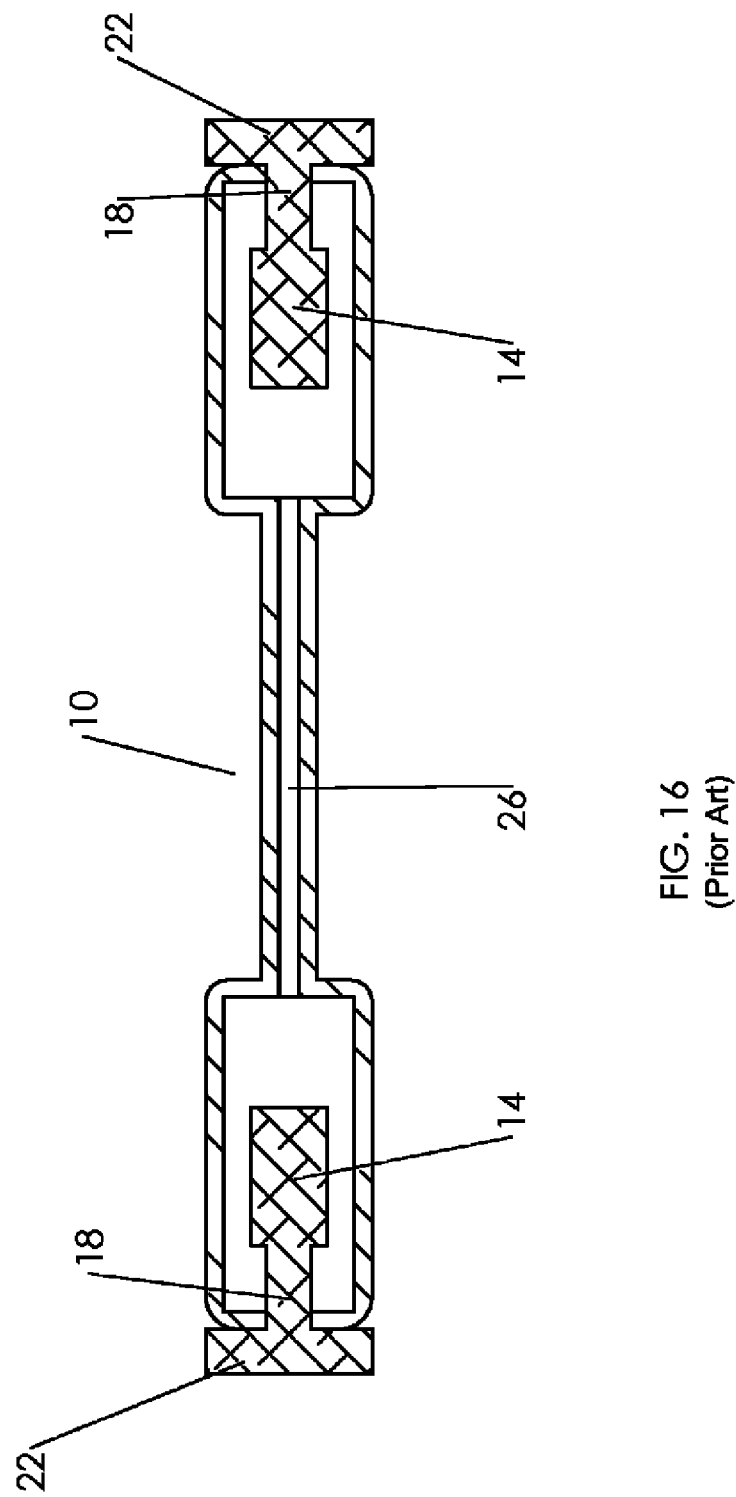
FIG. 16 is a cross sectional view of a prior art glass envelope for use with a prior art power unit.

Both the power unit 106A and the power unit 106B include an electrical circuit 760 as shown by the schematic of FIG. 15A. The electrical circuit 760 includes the power supply 322; the switch 346; the switch 640; the contacts 352A, 352B or the contacts 712A, 712B; the cartridge 112; a fuse 766; and a power supply 772. The electrical circuit 760 of the power unit 106B may be connected to a source of alternating current as represented by the mains power source 778, which, for example, may have an output voltage of 110 volts or 220 volts, as is commonly available at a wall outlet in most laboratories and educational environments (as shown in FIG. 15B). The power source 778 is connected to an input of the power supply 772. An output of the power supply 772 is connected to a serial arrangement of the switch 640, the switch 346, the fuse 766, and an input of the power supply 332. An output of the power supply 332 is connected to the contacts 712A, 712B or the contacts 352A, 352B, which may be connected to the cartridge 112. The electrical circuit 760 selectively couples electrical energy to the envelope 118 of the cartridge 112 received fully by the power unit 106B and the cartridge 112 in the active position of the power unit 106A.

The power supply 772 converts the alternating current signal received from the power source 788 to a direct current signal limited to approximately one thousand milliamps ("mA"). The direct current signal may have a voltage of approximately twelve volts to fifteen volts. The power supply 772 may be a commercially available A/C adapter, transformer unit, or switching power supply, as is known in the art.

The power supply 322 converts the direct current signal generated by the power supply 772 into an output signal. The output signal is an alternating current signal having a current of up to 20 milliamps and a frequency between approximately 20 kilohertz and 80 kilohertz ("kHz"). Additionally, the output signal has a root mean square voltage of between approximately 500 and 8000 volts. In particular, the output signal may couple between 2000 volts and 8000 volts to the contacts 352A, 352B in order to strike a discharge in a fluid contained by the envelope 118. Once the discharge is struck, the power supply 322 may couple between 800 volts and 1500 volts to the fluid in order to maintain the discharge. As shown in FIG.

15A, the input of the power supply 322 is connected to the output of the power supply 772. Alternatively, the input of the power supply 322 may be connected directly to the power source 788. The power supply 322 may be a commercially available power supply. Additionally, the power supply 322 may include an integrated voltage controller (not illustrated) for controlling the voltage output, as is known in the art.

The output signal of the power supply 322 is electrically connected to the fluid contained by the envelope 118 of the cartridge 112. In particular, in response to the output signal being supplied to the electrodes 124A, 124B, the voltage strikes a discharge in the fluid contained within the cavity 178. The current provided by the output signal of the power supply 322 maintains the discharge until one of the switch 640 or the switch 346 enters an "off" position. It is the high frequency, approximately 20 kilohertz to 80 kilohertz of the current signal, among other factors, that enables electrical energy from the power supply 322 to be connected to the fluid.

The switch 346 is a single pole single throw ("SPST") switch movable by a user via an actuator between "on" and "off" positions to enable or disable current flow.

The switch 640 is also a single pole single throw ("SPST") switch that is movable between an "on" position and an "off" position. The switch 640 is normally in the off position, and does not include a manually operated actuator. Instead, in the presence of the signaler 148, the switch 640, sometimes referred to as a detector, enters the on position, and in the absence of the signaler 148 the switch 640 enters the off position. To this end, the switch 640 may be a magnetic reed switch and the signaler 148 a magnet, as is known in the art. In response to either the switch 640 or the manual switch 346 being in the off position electrical energy is not supplied to the cartridge 112.

The switch 640 and the signaler 148 operate as a safety unit. In particular, with regard to the power unit 106A, the switch 640 in the off position prevents a voltage from being connected to the contacts 352A, 352B, even if the switch 346 is in the on position. With regard to the power unit 106B, the switch 640 in the off position prevents a voltage from being electrically connected to the contacts 712A, 712B, even if the switch 346 is in the on position. As shown in FIG. 15A, current may not flow though the cartridge 112 unless both the switch 640 and the switch 346 are in the on position. The switch 346 may moved to the on position by a user; however, the switch 640 is concealed from a user of the power unit 106A, 106B and may not be manually moved between the on and off positions. Instead, the signaler 148 operates the switch 640. In particular, with regard to the power unit 106A, the signaler 148 causes the switch 640 to enter the on position when a cartridge 112, fully received by a sleeve 358, is moved to the active position. With regard to the power unit 106B, the signaler 148 causes the switch 640 to enter the on position when a cartridge 112 is fully received by the receiver 682.

The fuse 766 limits the current flowing from the power supply 322, through the switch 640, the switch 346, and the cartridge 112. An exemplary fuse 766 may have a current rating of approximately one ampere and a voltage rating of approximately two hundred and fifty volts.

The power unit 106A may be operated according to the process described below. First, the carousel 310 is rotated such that one of the apertures 412 is positioned directly below the aperture 364. Next, a cartridge 112 is loaded into the sleeve 358 associated with the aperture 364. In particular, the cartridge 112 is positioned in the unique orientation, which enables the cartridge to pass through the aperture 364 and the aperture 412 and into the sleeve 358. The carousel 310 may be rotated to allow additional cartridges 112 to be loaded into the other sleeves 358. Next, with the switch 346 in the off position, the carousel 310 is rotated to position one of the cartridges 112 in the active position. In response to the cartridge 112 being moved to the active position, the contacts 142A, 142B are electrically connected to the contacts 352A, 352B. Additionally, the signaler 148, usually a magnet, is positioned to cause the switch 640 to enter the on position. To energize the fluid, the switch 346 is moved to the on position. Closing the switch 346 allows current from the power supply 322 to be electrically connected to the cartridge 112. In particular, the electrical energy from the power supply 322 is electrically connected to the fluid through the electrodes 124A, 124B to cause the fluid to emit light. The switch 346 may be moved to the off position to cause the fluid to cease emitting light. If a user positions the switch 346 in the on position but a cartridge 112 is not positioned in the active position, electrical energy is not electrically connected to the contacts 352A, 352B, because the signaler 148 is not in a position that causes the switch 640 to enter the on position.

The power unit 106B may be operated according to the process described below. First, with the switch 346 in the off position, the cartridge 112 is loaded into the receiver 682. In particular, the cartridge 112 is positioned in the unique orientation, which enables the cartridge to be received by the receiver 682. In response to the cartridge 112 being received by the receiver 682, the signaler 148 is positioned near the switch 640, and causes the switch 640 to enter the on position. Additionally, in response to the cartridge 112 being received by the receiver 682 the contacts 712A, 712B are electrically connected to the contacts 142A, 142B. To energize the fluid in the cartridge 112, the switch 346 is moved to the on position. In particular, electrical energy from the power supply 322 is electrically connected to the fluid through the electrodes 124A, 124B to cause the fluid to emit light as visible through the capillary portion 166 of the envelope 118. The switch 346 may be moved to the off position to cause the fluid to cease emitting light. If a user positions the switch 346 in the on position but a cartridge 112 is not received by the receiver 682, electrical energy is not connected to the contacts 712A, 712B. Therefore, a user may insert and remove cartridges 112 from the receiver 682 with the switch 346 remaining in the on position.

The tool holder 702 may be connected or coupled to the front plate 694 to position a tool to receive the light emitted by the energized envelope 118. The tool holder 702 may hold, for instance, the end of a fiber optic digital spectrometer sensor cable in the appropriate position for receiving the light emitted by the envelope 118.

The device described herein has been illustrated and described in detail in the figures and foregoing description, the same should be considered as illustrative and not restrictive in character. It is understood that only the preferred embodiments have been presented and that all changes, modifications, and further applications that come within the spirit of the device described herein are desired to be protected.

What is claimed is:

1. A spectral analysis apparatus, comprising:
  a light transmissive envelope including a first end portion and a second end portion, said envelope containing a fluid operable to emit light when electrically energized;
  a first electrode disposed upon an external surface of said first end portion, said first electrode being completely external to said envelope;
  a second electrode disposed upon an external surface of said second end portion, said second electrode being completely external to said envelope;

a cartridge configured to at least partially encase said envelope, said cartridge defining first and second openings therethrough;
a sleeve defining a cavity configured to removably receive said cartridge therein;
a first electrical contact associated with said cavity, said first electrical contact configured to electrically connect to said first electrode when said envelope is within said sleeve;
a second electrical contact associated with said cavity, said second electrical contact configured to electrically connect to said second electrode when said envelope is within said sleeve;
a third electrical contact associated with said cartridge, said third electrical contact being electrically connected to said first electrode and arranged to contact said first electrical contact when said cartridge is within said cavity; and
a fourth electrical contact associated with said cartridge, said fourth electrical contact being electrically connected to said second electrode and arranged to contact said second electrical contact when said cartridge is within said cavity;
a first spring positioned between and electrically connecting said third electrical contact and said first electrode, said first spring biasing said third electrical contact through said first opening; and
a second spring positioned between and electrically connecting said fourth electrical contact and said second electrode, said second spring biasing said fourth electrical contact through said second opening,
wherein said first electrical contact and said second electrical contact are connectable to an electrical power supply, and
wherein said electrodes electrically energize said fluid when electrically connected to said electrical power supply.

2. The spectral analysis apparatus of claim 1, wherein said first end portion of said envelope is fluidly coupled to said second end portion of said envelope with a capillary portion, and said cartridge includes a window configured to expose only said capillary portion.

3. The spectral analysis apparatus of claim 1, wherein said electrical power supply has a voltage between 500 volts and 8000 volts and a current of at most approximately 20 milliamps.

4. The spectral analysis apparatus of claim 1, further comprising:
a first transformer unit configured to transform a first power level from a mains power supply to a second power level, said second power level supplying a first voltage and a first current,
wherein said electrical power supply is a second transformer unit configured to transform said second power level to a third power level, said third power level supplying a second voltage and a second current,
wherein said first voltage is approximately 12 to 15 volts and said first current is approximately 500 to 1000 milliamps direct current,
wherein said second voltage is between 500 and 8000 volts and said second current is approximately 20 milliamps alternating current, said second current having a frequency between 20 kilohertz to 80 kilohertz.

5. A spectral analysis apparatus, comprising:
a light transmissive envelope including a first end portion and a second end portion, said envelope containing a fluid operable to emit light when electrically energized;
a first electrode disposed upon an external surface of said first end portion, said first electrode being completely external to said envelope;
a second electrode disposed upon an external surface of said second end portion, said second electrode being completely external to said envelope;
a cartridge configured to at least partially encase said envelope;
a sleeve defining a cavity configured to removably receive said cartridge therein;
a first electrical contact associated with said cavity, said first electrical contact configured to electrically connect to said first electrode when said envelope is within said sleeve;
a second electrical contact associated with said cavity, said second electrical contact configured to electrically connect to said second electrode when said envelope is within said sleeve;
a first annular plate positioned at a first end of said sleeve, said first annular plate defining a first central opening; and
a second annular plate positioned at a second end of said sleeve, said second annular plate including a cartridge aperture and defining a second central opening,
wherein said first electrical contact and said second electrical contact are connectable to an electrical power supply,
wherein said electrodes electrically energize said fluid when electrically connected to said electrical power supply, and
wherein said cartridge defines a longitudinal axis between a first end of said cartridge and a second end of said cartridge and said cartridge moves through said cartridge aperture in a first direction to be received within said cavity, said first direction is approximately parallel to said longitudinal axis.

6. The spectral analysis apparatus of claim 5, wherein said cartridge defines an irregular periphery and said cartridge aperture defines said irregular periphery, said cartridge being movable through said cartridge aperture in only one orientation.

7. A spectral analysis apparatus, comprising:
a cartridge including a light transmissive envelope having a first electrode and a second electrode, said first electrode being completely external to said envelope, and said second electrode being completely external to said envelope, said envelope containing a fluid operable to emit light when electrically energized;
a carousel including a plurality of sleeves, each sleeve including a first contact opening and a second contact opening, and each sleeve being configured to receive said cartridge; and
a base including a first electrical contact and a second electrical contact, said carousel being movably supported on said base,
wherein said first electrical contact and second electrical contact are connectable to an electrical power supply,
wherein said carousel is movable relative to said base to position one of said sleeves in an active position in which (i) said first contact opening of said one of said sleeves is positioned to receive said first electrical contact and (ii) said second contact opening of said one of said sleeves is positioned to receive said second electrical contact,
wherein in response to said cartridge being received by said sleeve in said active position, said first electrical contact electrically connects to said first electrode and said second electrical contact electrically connects to said second electrode, and wherein said first electrode and said second electrode electrically energize said fluid when electrically connected to said electrical power supply.

8. The spectral analysis apparatus of claim 7, wherein each of said sleeves other than said sleeve in said active position is in an inactive position, said first contact openings of said sleeves in said inactive position are displaced from said first electrical contact and second contact openings of said sleeve in said inactive position are displaced from said second electrical contact.

9. The spectral analysis apparatus of claim 8, further comprising:
   a first biasing spring mounted to said base, said first biasing spring configured to bias said first electrical contact through said first contact opening of said sleeve in said active position; and
   a second biasing spring mounted to said base, said second biasing spring configured to bias said second electrical contact through said second contact opening of said sleeve in said active position,
   wherein said electrical power supply is electrically connected to said first electrical contact through said first biasing spring, and said electrical power supply is electrically connected to said second electrical contact through said second biasing spring.

10. The spectral analysis apparatus of claim 9, further comprising:
    a third electrical contact electrically connected to said first electrode; and
    a fourth electrical contact electrically connected to said second electrode,
    wherein said third electrical contract is electrically connected to said first electrical contact in response to said sleeve receiving said cartridge and being in said active position, and said fourth electrical contact is electrically connected to said second electrical contact in response to said sleeve receiving said cartridge and being in said active position.

11. The spectral analysis apparatus of claim 8, wherein only said sleeve in said inactive position is configured to received said cartridge.

12. The spectral analysis apparatus of claim 7, further comprising:
    a cap member connected to said base, said cap member defining an aperture,
    wherein said sleeve in said inactive position is aligned with said aperture such that said cartridge passes completely through said aperture before being received by said sleeve in said active position.

13. The spectral analysis apparatus of claim 12, wherein said cartridge defines an irregular periphery and said aperture defines said irregular periphery, said cartridge passing through said aperture in only one orientation.

14. The spectral analysis apparatus of claim 7, further comprising:
    a tool member connectable to said base and configured to receive at least a portion of said light emitted by said fluid.

15. The spectral analysis apparatus of claim 7, wherein said carousel includes eight sleeves.

16. The spectral analysis apparatus of claim 7, further comprising:
    a safety element associated with one of said cartridge and said base, said safety element being in an engaged position in response to said cartridge being received by said sleeve in said active position; and
    a detector associated with the other of said cartridge and said base, said detector enabling electrical energy from said electrical power supply to be supplied to said first electrical contact and said second electrical contact in response to detecting said safety element being in said engaged position, and said detector preventing electrical energy from said electrical power supply from being electrically connected to said first electrical contact and said second electrical contact in response to said safety element being in a position other than said engaged position.

17. The spectral analysis apparatus of claim 16, wherein said safety element is a magnet connected to said cartridge and said detector is a reed switch connected to said base, said reed switch being closed when said magnet is in said engaged position and said reed switch being open when said magnet is in said position other than said engaged position.

18. A spectral analysis apparatus, comprising:
    a cartridge including a light transmissive envelope having a first electrode and a second electrode, said first electrode being completely external to said envelope, and said second electrode being completely external to said envelope, said envelope containing a fluid operable to emit light when electrically energized;
    a carriage defining a cavity, said carriage being configured to removably receive said cartridge within said cavity;
    a base unit including a guide structure, said carriage being movable relative to said base unit about said guide structure;
    a first electrical contact within said cavity, said first electrical contact configured to electrically connect to said first electrode when said cartridge is within said cavity;
    a second electrical contact within said cavity, said second electrical contact configured to electrically connect to said second electrode when said cartridge is within said cavity;
    a signaler associated with one of said cartridge and said cavity; and
    a detector associated with said other of said cartridge and said cavity, said detector being configured to detect said signaler,
    wherein said first electrical contact and said second electrical contact are connectable to an electrical power supply,
    wherein said electrodes electrically energize said fluid when electrically connected to said electrical power supply, and
    wherein said detector detects said signaler only in response to said cartridge being received completely by said cavity, said detector enables coupling of said electrical power supply to said first electrical contact and said second electrical contact in response to detecting said signaler, said detector prevents coupling of said electrical power supply to said first electrical contact and said second electrical contact in response to not detecting said signaler.

19. The spectral analysis apparatus of claim 18, the guide structure comprising:
    a first support shaft connected to said base unit, said first support shaft being configured to be movably received by a first shaft opening in said carriage; and
    a second support shaft connected to said base unit, said second support shaft configured to be movably received by a second shaft opening in said carriage.

20. The spectral analysis apparatus of claim 19, wherein said carriage moves vertically relative to said base unit about said first and second support shafts.

21. The spectral analysis apparatus of claim 18, wherein said cartridge defines an irregular periphery and said cavity defines said irregular periphery such that said cartridge is received in said cavity in only one orientation.

22. The spectral analysis apparatus of claim 18, said base unit further comprising:
a plurality of receptacles, each receptacle being configured to receive at least partially said cartridge, each of said receptacles defining an irregular periphery and said cartridge defining said irregular periphery such that said cartridge is receivable in said receptacle in only one orientation.

23. The spectral analysis apparatus of claim 18, wherein said signaler is a magnet associated with said cartridge and said detector is a reed switch associated with said cavity, said magnet closing said reed switch in response to said cartridge being received fully by said cavity.

24. The spectral analysis apparatus of claim 18, further comprising:
a tool member connectable to said carriage and configured to receive at least a portion of said light emitted by said fluid.

25. A spectral analysis apparatus, comprising:
a cartridge including a light transmissive envelope having a first electrode and a second electrode, said first electrode being completely external to said envelope, and said second electrode being completely external to said envelope, said envelope containing a fluid operable to emit light when electrically energized;
a receiver defining a cavity, said receiver being configured to removably receive said cartridge within said cavity;
a first electrical contact within said cavity, said first electrical contact configured to electrically connect to said first electrode when said cartridge is within said cavity;
a second electrical contact within said cavity, said second electrical contact configured to electrically connect to said second electrode when said cartridge is within said cavity;
a signaler associated with one of said cartridge and said receiver; and
a detector associated with said other of said cartridge and said receiver, said detector being configured to detect said signaler,
wherein said first electrical contact and said second electrical contact are connectable to an electrical power supply,
wherein said detector detects said signaler only in response to said cartridge being received completely by said cavity, said detector enables connecting of said electrical power supply to said first electrical contact and said second electrical contact in response to detecting said signaler, said detector prevents connecting of said electrical power supply to said first electrical contact and said second electrical contact in response to not detecting said signaler, and
wherein said electrodes electrically energize said fluid when electrically connected to said electrical power supply.

26. The spectral analysis apparatus of claim 25, wherein said detector is a reed switch associated with said receiver and said signaler is a magnet associated with said cartridge, said magnet closing said reed switch in response to said cartridge being received fully by said receiver.

27. The spectral analysis apparatus of claim 26, wherein said magnet is connected to an internal region of said cartridge.

28. The spectral analysis apparatus of claim 25, further comprising:
an aperture having an irregular periphery defined by said receiver,
wherein said cartridge defines said irregular periphery, and
wherein said cartridge further defines a longitudinal axis between a first end of said cartridge and a second end of said cartridge, such that said irregular periphery of said cartridge enables said cartridge to pass through said aperture only when said first end passes through said aperture before said second end passes through said aperture.

29. The spectral analysis apparatus of claim 25, wherein in response to said cartridge being received fully by said receiver none of said first electrical contact, said second electrical contact, said first electrode, said second electrode, said signaler, and said detector are accessible for contact by a user of said spectral analysis apparatus.

30. The spectral analysis apparatus of claim 29, wherein in response to said cartridge not being received fully by said receiver, said detector does not detect said signaler and said electrical power supply is disconnected from said first electrical contact and said second electrical contact before any of said first electrical contact, said second electrical contact, said first electrode, said second electrode, said signaler, and said detector are accessible for contact by a user of said spectral analysis apparatus.

* * * * *